(12) United States Patent
Kawai et al.

(10) Patent No.: US 7,860,607 B2
(45) Date of Patent: Dec. 28, 2010

(54) METHOD OF ESTIMATING JOINT MOMENT OF BIPEDAL WALKING BODY

(75) Inventors: Masakazu Kawai, Wako (JP); Yasushi Ikeuchi, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 877 days.

(21) Appl. No.: 10/564,073

(22) PCT Filed: Jun. 29, 2004

(86) PCT No.: PCT/JP2004/009516

§ 371 (c)(1),
(2), (4) Date: Jan. 10, 2006

(87) PCT Pub. No.: WO2005/005107

PCT Pub. Date: Jan. 20, 2005

(65) Prior Publication Data

US 2007/0084278 A1    Apr. 19, 2007

Related U.S. Application Data

(60) Provisional application No. 60/486,543, filed on Jul. 11, 2003.

(30) Foreign Application Priority Data

Sep. 11, 2003    (JP) ............................. 2003-320108

(51) Int. Cl.
*G06F 19/00* (2006.01)
*A61B 5/103* (2006.01)
(52) U.S. Cl. .......................... 700/245; 600/595; 73/172
(58) Field of Classification Search ................ 600/595; 700/425, 245; 73/172
See application file for complete search history.

(56) References Cited

U.S. PATENT DOCUMENTS

| 6,289,265 B1 * | 9/2001 | Takenaka et al. ............ 700/245 |
| 2003/0018283 A1 * | 1/2003 | Dariush ...................... 600/595 |
| 2003/0120388 A1 | 6/2003 | Kuroki et al. |

FOREIGN PATENT DOCUMENTS

| EP | 1 103 451 | 5/2001 |
| EP | 1 415 770 | 5/2004 |
| EP | 1 424 172 | 6/2004 |
| JP | 2003-089083 | 3/2003 |
| JP | 2003-117857 | 4/2003 |

OTHER PUBLICATIONS

Kato et al. "The Concept of a Walking Assistance Suit", The Japanese Society of Mechanical Engineers, Aug. 2001 as cited in the IDS for 10642477 doc C1.*

* cited by examiner

*Primary Examiner*—Max Hindenburg
*Assistant Examiner*—Renee Danega
(74) *Attorney, Agent, or Firm*—Rankin, Hill & Clark LLP

(57) ABSTRACT

The joint rotational angles of joints 9, 11 and 13 of each leg 2 of a bipedal walking body 1 are detected to grasp the positions/postures of the corresponding rigid bodies 10, 12 and 14 of each leg 2 on a leg plane passing the joints 9, 11 and 13 of each leg 2. At the same time, the acceleration of a reference point (the origin of a body coordinate system BC) of the bipedal walking body 1, the floor reaction force acting on each leg 2 and the position of an acting point thereof are grasped in terms of three-dimensional amounts. Two-dimensional amounts obtained by projecting the acceleration, the floor reaction force and the position of the acting point thereof, and the positions/postures of the corresponding rigid bodies of each 2 onto the leg plane are used to estimate the moments acting on joints of each leg on the basis of an inverse dynamic model. The stability of the estimated values of joint moments can be improved while securing the accuracy of estimating the joint moments in the bending and stretching directions of each leg, considering three-dimensional motions of the bipedal walking body.

7 Claims, 20 Drawing Sheets

METHOD OF ESTIMATING JOINT MOMENT OF BIPEDAL WALKING BODY

TECHNICAL FIELD

The present invention relates to a method of estimating the moment (joint moment) acting on a joint of each leg of a bipedal walking body, such as a human being or a bipedal walking robot.

BACKGROUND ART

To control an operation of, for example, a walking aid apparatus for assisting a human being in walking, it is necessary to grasp the joint moments actually acting on joints of legs of the human being. Grasping the joint moments makes it possible to properly determine desired auxiliary forces of the walking aid apparatus. In a bipedal walking robot also, there are cases where it is required to grasp a joint moment actually acting on each joint of a leg to conduct the operation control.

Hence, the present applicant has previously proposed in, for example, Japanese Unexamined Patent Application Publication No. 2003-89083 (hereinafter referred to as Patent Document 1), a technique for estimating a joint moment of a leg of a bipedal walking body, such as a human being. According to this technique, a displacement amount (rotational angle) of each joint of a leg of the bipedal walking body, the acceleration of a predetermined part, and angular velocity are measured using required sensors, and then the measurement data and a rigid link model of the bipedal walking body or the like are used to estimate a floor reaction force (translational floor reaction force) acting on each leg and the position of an acting point thereof. Here, the rigid link model is a model representing a structure of the bipedal walking body in terms of an assembly formed by connecting a plurality of rigid elements by a plurality of joint elements. The rigid link model is used to estimate the position of the overall center-of-gravity of the bipedal walking body, the positions and the postures of corresponding rigid bodies of the bipedal walking body (thighs, cruses, waist, etc.) respectively associated with the rigid elements and the joint elements, and the positions and the postures of joints (knee joints, hip joints, etc.), and it is also used as the basis of the model for describing a dynamic behavior of the bipedal walking body. In the rigid elements of the rigid link model, the weights, the lengths, and the positions of the centers of gravity thereof (the positions on the rigid elements) are collaterally set beforehand.

And, according to the one in Patent Document 1 mentioned above, the estimated floor reaction force and the position of the acting point thereof and the rigid link model are used to estimate the joint moments of the knee joints or the hip joints of the legs by arithmetic processing based on an inverse dynamic model. The inverse dynamic model is generally described as a dynamic model for estimating a reaction force or a moment, which is an internal force of an object, an external force acting on the object and positional information being known (the external force and the positional information being input parameters), and it represents the relationship between motions of the object (a positional time-series pattern) and forces or moments acting on the object. According to the technique in Patent Document 1 mentioned above, the inverse dynamic model is constructed on the basis of dynamic equations related to motions (translational motions and rotational motions) of the rigid elements of the rigid link model, and joint moments of each leg are estimated in order, the moment of the joint closest to the acting point of a floor reaction force being the first to be estimated.

When assisting a human being as a bipedal walking body with walking, it is desired to estimate the joint moment of each joint with high accuracy especially in the direction in which a leg bends or stretches in order to precisely perform the assistance of the walking. For this reason, according to an embodiment of the one in the Patent Document 1 mentioned above, the motion (two-dimensional motion) of a human being on the plane (sagittal plane) of a vertical posture with the lateral direction of the human being defined as a normal line direction is grasped so as to estimate a joint moment (a moment about a lateral axis).

However, joints, such as a hip joint, of a leg of the human being are capable of three-dimensional (spatial) motions, including the motions of a leg in the bending and stretching directions, and they are capable of a motion of, for example, moving each leg in the lateral directions by rotation about a substantially longitudinal axis of a hip joint (so-called abduction and adduction) or a twisting motion (turning motion) of each leg by rotation about a substantially vertical axis of the hip joint. Therefore, there are many cases where bending motions of the legs are not performed on the sagittal plane of a vertical posture when a human being moves. In such cases, there has been likelihood that the accuracy of estimating joint moments in the bending/stretching directions of the legs deteriorates in an embodiment of Patent Document 1 mentioned above.

Considering the three-dimensional motions of the legs described above, in order to accurately estimate the joint moments of the legs of a bipedal walking body as much as possible, it is considered desirable to grasp the motions of parts of the bipedal walking body (the positions, postures, accelerations, and the like of corresponding rigid bodies) and the floor reaction force acting on each leg of the bipedal walking body and the position of the acting point thereof in terms of three-dimensional amounts (a set of coordinate component values in a given three-dimensional coordinate system) so as to estimate a joint moment of a leg on the basis of the grasped values.

However, in this case, it is necessary to grasp, using appropriate sensors, the three-dimensional displacement amounts of the hip joints, the knee joints and ankle joints of the legs. And, in particular, the joints of the legs of the human being as a bipedal walking body are capable of performing complicated motions and are apt to be subject to restrictions on the mounting locations or mounting forms of the sensors for detecting the displacement amounts. For this reason, it is usually difficult to grasp every component of the three-dimensional displacement amounts of the joints with sufficiently high accuracy. Further, the accuracy of the displacement amount of a joint grasped from an output of a sensor tends to vary, depending on a posture state or the like of a leg.

Hence, even if an attempt is made to estimate a joint moment in the bending/stretching directions of a leg by simply using a three-dimensional technique, there has been a danger in that an error inconveniently increases or an estimated value thereof inconveniently tends to suddenly changes (the robust performance deteriorates).

The present invention has been made in view of the above background, and it is an object of the present invention to provide a method of estimating a joint moment of a bipedal walking body that permits enhanced stability of an estimated value of a joint moment in bending/stretching directions of a leg, while securing estimation accuracy, considering three-dimensional motions of the bipedal walking body.

DISCLOSURE OF INVENTION

A variety of studies and experiments conducted by the inventors of the present application has revealed that the motions in the bending/stretching directions of each leg of a bipedal walking body, such as a human being, are performed on a plane that passes through three joints, a hip joint, a knee joint and an ankle joint of the leg. To estimate a joint moment in the bending or stretching direction of each leg, the joint moment about an axis in the direction that is substantially perpendicular to the aforesaid plane (hereinafter referred to as the leg plane in some cases) may be estimated. In this case, the spatial posture (the direction of the normal line) of the leg plane will be based on a three-dimensional displacement amount of a hip joint although it is not necessarily a vertical posture. Of the three-dimensional displacement amounts of the joints, namely, the hip joint, the knee joint and the ankle joint, of a leg, at least a rotational angle about the axis that is substantially perpendicular to the leg plane can be grasped with relatively high accuracy by using a sensor, such as a potentiometer or a rotary encoder.

Accordingly, a method of estimating a joint moment of a bipedal walking body in accordance with the present invention includes a first step for sequentially grasping the displacement amounts of a plurality of joints, including at least an ankle joint, a hip joint and a knee joint of each leg of a bipedal walking body, a second step for sequentially grasping the positions and/or postures of corresponding rigid bodies of the bipedal walking body that are associated with rigid elements of a rigid link model by using at least the rigid link model wherein the rigid link model being established beforehand to express the bipedal walking body in the form of a link assembly composed of a plurality of the rigid elements and a plurality of joint elements and the grasped displacement amounts of the joints, a third step for grasping the acceleration of a preset reference point of the bipedal walking body by using at least an output of an acceleration sensor attached to a predetermined region of the bipedal walking body, and a fourth step for sequentially grasping a floor reaction force acting on each leg and the position of an acting point of the floor reaction force, wherein the grasped positions and/or the postures of the corresponding rigid bodies of the bipedal walking body, the acceleration of the reference point, the floor reaction force, and the position of the acting point of the floor reaction force are used to estimate a joint moment acting on at least one joint of each leg, at least the displacement amounts of the hip joint, the knee joint, and the ankle joint of each leg that are grasped in the first step include the amount of rotation about an axis substantially perpendicular to a leg plane as a plane passing through these three joints, the displacement amount of the hip joint is a three-dimensional amount, the positions and/or postures of the corresponding rigid bodies grasped in the second step include at least the positions and/or the postures of the corresponding rigid bodies of the leg on the leg plane, the acceleration of the reference point grasped in the third step and the floor reaction force and the position of the acting point of the floor reaction force grasped in the fourth step are three-dimensional amounts, and a component of a joint moment acting on at least one joint of the leg about the axis that is substantially perpendicular to the leg plane is estimated on the basis of an inverse dynamic model representing the relationship between the motions of the corresponding rigid bodies of the leg and the translational forces and the moments acting on the corresponding rigid bodies on the leg plane by using the two-dimensional amounts obtained by projecting at least the acceleration of the reference point, the floor reaction force, and the position of the acting point of the floor reaction force onto a leg plane related to the leg on the basis of a displacement amount of the hip joint of the leg, and the positions and/or the postures of the corresponding rigid bodies of the leg on the leg plane (first invention).

Basically any techniques may be used to grasp the floor reaction forces and the acting points thereof. For instance, load sensors or pressure distribution sensors may be attached to the soles of the feet of the legs thereby to grasp floor reaction forces or the positions of the acting points thereof from the outputs of the sensors. Alternatively, a bipedal walking body may move on a floor provided with a force plate having load sensors so as to grasp floor reaction forces or the positions of the acting points thereof from the outputs of the force place. Alternatively, the techniques to be explained in third to seventh inventions, which will be discussed later, may be used to grasp floor reaction forces and the positions of the acting points thereof.

According to the first invention described above, the amounts of rotations of the hip joint, the knee joint, and the ankle joint of the leg about the axis that is substantially perpendicular to the leg plane, which are grasped in the first step, can be grasped with relatively high accuracy by using potentiometers or rotary encoders, as described above. Hence, the positions and/or the postures of corresponding rigid bodies of each leg on a leg plane (the leg plane corresponding to the leg) can be grasped with relatively high accuracy without depending on the three-dimensional motions, including motions (abduction, external rotation, adduction, internal rotation and the like of each leg) other than two-dimensional motions of each leg on the leg plane. Further, the acceleration of the reference point of the bipedal walking body and the floor reaction force acting on each leg and the position of the acting point thereof are grasped in terms of three-dimensional amounts (vector amounts represented by a certain three-dimensional coordinate system), considering the spatial motions of the bipedal walking body, and then they are projected onto a leg plane related to the leg on the basis of the displacement amount (three-dimensional amount) of the hip joint of the leg so as to obtain the two-dimensional amounts of the acceleration of the reference point and the floor reaction force and the acting point thereof on the leg plane (technically, the components on a plane parallel to the leg plane). Then, the two-dimensional amounts of the acceleration of the reference point and the floor reaction force and the acting point thereof on the leg plane and the positions and/or the postures of the corresponding rigid bodies on the leg plane grasped as described above are used to estimate a component of the joint moment acting on at least one joint of the leg on the basis of an inverse dynamic model on the leg plane, the component being the one about an axis that is substantially perpendicular to the leg plane. In this case, even if a component of the displacement amount of a hip joint of the leg grasped in the first step, which component is other than the amount of rotation about the axis that is substantially perpendicular to the leg plane, has an error, at least the positions and/or the postures of the corresponding rigid bodies of the leg on the leg plane, which are used for the computation of the inverse dynamic model, can be grasped with high accuracy, as described above. This makes it possible to estimate the component of the joint moment about the axis that is substantially perpendicular to the leg plane with satisfactory estimation accuracy and also to prevent the component from excessively varying.

Thus, according to the present invention, the stability of estimated values can be enhanced while considering three-dimensional motions of a bipedal walking body and securing the estimation accuracy of joint moments in the bending and stretching directions of each leg.

Supplementally, projecting the acceleration of the reference point, the floor reaction force, and the position of the acting point of the floor reaction force mentioned above onto the leg plane is equivalent to coordinate-converting the vector of the acceleration, the vector of the floor reaction force, and the vector of the position of the acting point, which are expressed in terms of an arbitrary three-dimensional coordinate system, into vector amounts expressed in terms of a three-dimensional coordinate system that includes the leg plane as one coordinate plane, and then extracting the components of the leg plane of the vector amounts.

The region of the bipedal walking body where the acceleration sensor is installed and the region where the reference point is set may be different from each other; however, it is basically preferred that they are installed in the same region (a corresponding rigid body associated with a certain rigid element of the rigid link model), and it is particularly preferred that the part is the waist.

Further, in the first invention, the acceleration of the reference point grasped in the third step, and the floor reaction force and the position of the acting point of the floor reaction force grasped in the fourth step are preferably three-dimensional amounts expressed in terms of a body coordinate system set beforehand as a three-dimensional coordinate system fixed to one predetermined rigid element of the rigid link model (a second invention).

More specifically, the three-dimensional amounts of the acceleration of the reference point, etc. may be basically expressed by any three-dimensional coordinate system. If, for example, they are expressed by a three-dimensional coordinate system that includes a vertical axis and a horizontal axis, then it is necessary to grasp an inclination angle of a corresponding rigid body of the bipedal walking body relative to the vertical direction by using an inclination sensor, such as a gyro sensor. The inclination sensor, however, is usually apt to incur an integral error or an error caused by an influence of inertial acceleration due to a motion of the bipedal walking body. For this reason, it is desirable to estimate a joint moment without using the information on an inclination of a portion of the bipedal walking body as much as possible. Hence, according to the second invention, the acceleration of the reference point, the floor reaction force, and the position of the acting point of the floor reaction force are grasped as three-dimensional amounts in the body coordinate system. Thus, a joint moment is estimated by grasping the acceleration of the reference point, etc. in terms of three-dimensional amounts in the body coordinate system, making it possible to minimize the arithmetic processing that uses inclination information of the bipedal walking body. As a result, causes for errors in estimating joint moments are lessened, allowing the accuracy of the estimated value to be secured. In fourth to sixth inventions to be described later, grasping the position of the acting point of a floor reaction force requires the information on the inclination angle (the inclination angle relative to the vertical direction) of a certain corresponding rigid body of the bipedal walking body. In this case also, the acceleration of the reference point and a floor reaction force can be grasped as three-dimensional amounts in a body coordinate system without using information on an inclination angle.

In the second invention described above, the value of a floor reaction force in the body coordinate system (three-dimensional amount) can be grasped also, for example, from outputs of a load sensor or a pressure distribution sensor attached to the sole of a foot portion of a bipedal walking body. However, if the bipedal walking body is a human being, in particular, then a load sensor or the like attached to sole of a foot portion tends to interfere with smooth walking. In a third invention, therefore, the values of floor reaction force vectors in the body coordinate system are grasped by, for example, the following technique.

The technique includes a fifth step for sequentially determining the position of the overall center-of-gravity of the bipedal walking body in the body coordinate system by using the displacement amounts of joints of the bipedal walking body grasped in the first step and by using the rigid link model, a sixth step for sequentially determining the acceleration of the overall center-of-gravity on the body coordinate system from the time series data of the position of the overall center-of-gravity and the acceleration of the origin of the body coordinate system grasped using at least an output of the acceleration sensor, and a seventh step for sequentially determining whether a motion state of the bipedal walking body is a one-leg supporting state in which only one of a pair of legs is in contact with the ground or a two-leg supporting state in which both legs are in contact with the ground. If the motion state of the bipedal walking body is the one-leg supporting state, then the fourth step estimates the value of a floor reaction force on the body coordinate system according to a dynamic equation of the overall center-of-gravity of the bipedal walking body expressed by the acceleration of the overall center-of-gravity determined in the sixth step, the total weight of the bipedal walking body, and the floor reaction force acting on the leg in contact with the ground. If the motion state of the bipedal walking body is the two-leg supporting state, then the fourth step grasps the values of the floor reaction forces acting on the two legs, respectively, in the body coordinate system, on the basis of a dynamic equation of the overall center-of-gravity of the bipedal walking body expressed by the acceleration of the overall center-of-gravity determined in the sixth step, the total weight of the bipedal walking body, and the floor reaction force acting on the two legs, respectively, and the expression of the relationship between the relative position of a specific part of the leg with respect to the overall center-of-gravity of the bipedal walking body and the floor reaction forces acting on the leg, which is established on the assumption that the floor reaction forces acting on the legs are the vectors acting toward the overall center-of-gravity of the bipedal walking body from the specific part specified beforehand in the vicinity of the bottom end of the leg (a third invention).

With this arrangement, the floor reaction force acting on the leg in contact with the ground is determined on the basis of the dynamic equation of the overall center-of-gravity (the dynamic equation related to the translational motion of the overall center-of-gravity) of the bipedal walking body in the one-leg supporting state and the two-leg supporting state. Hence, floor reaction forces can be estimated without using load sensors or the like that would interfere with or add load to the walking of the bipedal walking body. In the two-leg supporting state, a floor reaction force acting on each of the legs cannot be identified by using only the dynamic equation of the overall center-of-gravity (the dynamic equation related to the translational motion of the overall center-of-gravity); however, the floor reaction force of each leg can be estimated by additionally using the expression of the relationship between the relative position of a specific part of the leg with respect to the overall center-of-gravity of the bipedal walking body and the floor reaction forces acting on the leg, which is established on the assumption that the floor reaction forces acting on the legs are the vectors acting toward the overall center-of-gravity of the bipedal walking body from the specific part (e.g., the ankle joint of each leg or a floor reaction force acting point) specified beforehand in the vicinity of the bottom end of the leg. In this case, regarding the acceleration of the overall center-of-gravity of the bipedal walking body necessary for the dynamic equation, the values in the body coordinate system thereof are sequentially determined, so that the dynamic equation of the overall center-of-gravity can be described simply by coordinate component values of a body coordinate system. The expression of relationship between the relative position of a specific part of the leg with respect to the overall center-of-gravity of the bipedal walking body and the floor reaction forces acting on the leg can be described simply by coordinate component values of the body coordinate system. Thus, the value (three-dimensional amount) of a floor reaction force on a body coordinate system can be determined without grasping the inclination state (the inclination state relative to the vertical direction) of a corresponding rigid body to which a body coordinate system is fixed.

The acting points of floor reaction forces can be estimated by, for example, attaching pressure distribution sensors to the soles of the feet of a bipedal walking body so as to use their detection outputs; they can be also estimated by, for example, the following technique.

The technique includes an eighth step for sequentially grasping the inclination angle of a corresponding rigid body of a bipedal walking body relative to the vertical direction, which corresponds to one predetermined rigid element of the rigid link model, a ninth step for determining whether each of the legs of the bipedal walking body is in contact with the ground, and a tenth step for grasping the positional relationship among at least the overall center-of-gravity of the bipedal walking body, the ankle joint of each leg in contact with the ground, and the metatarsophalangeal joint of the foot portion of the leg, and the vertical position of the ankle joint by using the inclination angle grasped in the eighth step, a displacement amount of each joint of the bipedal walking body grasped in the first step, and the rigid link model. The fourth step estimates the position in a horizontal plane of the acting point of a floor reaction force acting on a leg on the basis of the positional relationship among the overall center-of-gravity, the ankle joint of each leg in contact with the ground and the metatarsophalangeal joint of the foot portion of the leg grasped in the tenth step, and also estimates the vertical position of the acting point of a floor reaction force acting on the leg on the basis of the vertical position of the ankle joint of the leg (a fourth invention).

In other words, the position of the acting point in the horizontal plane of a floor reaction force acting on a leg of the bipedal walking body, the leg being in contact with the ground, is closely connected with the relative positional relationship among the ankle joint and the metatarsophalangeal joint of the foot portion of the leg, and the overall center-of-gravity of the bipedal walking body. Further, the vertical position of the acting point of a floor reaction force has a substantially constant correlation with the vertical position of an ankle joint of a leg. Therefore, it is possible to estimate the position in a horizontal plane of an acting point of a floor reaction force acting on a leg on the basis of the positional relationship among the overall center-of-gravity of the bipedal walking body, the ankle joint of each leg in contact with the ground and the metatarsophalangeal joint of the foot portion of the leg, and also to estimate the vertical position of the acting point of a floor reaction force acting on the leg on the basis of the vertical position of the ankle joint of the leg. In this case, the positional relationship among the overall center-of-gravity of the bipedal walking body, the ankle joint of each leg in contact with the ground and the metatarsophalangeal joint of the foot portion of the leg, and the vertical position of the ankle joint can be grasped by using the inclination angle of the corresponding rigid body of the bipedal walking body relative to the vertical direction grasped in the eighth step, the displacement amount of each joint of the bipedal walking body grasped in the first step, and the rigid link model.

Grasping the acting point of a floor reaction force as described above makes it possible to grasp the acting point of a floor reaction force without installing pressure distribution sensors on the soles of the feet of legs. Moreover, the elimination of need for installing pressure distribution sensors on the soles of the feet to which relatively high load tends to be instantly applied provides an advantage in the aspect of durability of an apparatus configuration for estimating joint moments.

The fourth invention may be combined with the second invention or the third invention. In this case, the position of the acting point of a floor reaction force on the body coordinate system can be determined by grasping the position in a horizontal plane and the vertical position of the acting point of the floor reaction force as described above, and then by using at least the position in the horizontal plane, the vertical position, and the inclination angle grasped in the eighth step.

According to the fourth invention, the position in the horizontal plane (the position in a longitudinal direction and a lateral direction of the bipedal walking body) of the acting point of a floor reaction force can be grasped as described below. If the overall center-of-gravity exists at the rear side of the bipedal walking body in the longitudinal direction with respect to the ankle joint of the leg in contact with the ground, then the fourth step estimates the position in the horizontal plane of the ankle joint of the leg (the position in the longitudinal direction and the lateral direction) as the position in the horizontal plane (the position in the longitudinal direction and the lateral direction) of the acting point of the floor reaction force acting on the leg; if the overall center-of-gravity exists at the front side of the bipedal walking body in the longitudinal direction with respect to the metatarsophalangeal joint of the foot portion of the leg in contact with the ground, then the fourth step estimates the position in the horizontal plane of the metatarsophalangeal joint of the foot portion of the leg (the position in the longitudinal direction and the lateral direction) as the position in the horizontal plane (the position in the longitudinal direction and the lateral direction) of the acting point of the floor reaction force acting on the leg; and if the overall center-of-gravity exists at the front side of the bipedal walking body in the longitudinal direction with respect to the ankle joint of the leg in contact with the ground and exists at the rear side with respect to the metatarsophalangeal joint of the foot portion of the leg at the same time, then the fourth step estimates the position of a point in the horizontal plane (the position in the longitudinal direction and the lateral direction), at which its longitudinal position agrees with the overall center-of-gravity on a segment that connects the ankle joint and the metatarsophalangeal joint of the leg, as the position in the horizontal plane (the position in the longitudinal direction and the lateral direction) of the acting point of the floor reaction force acting on the leg (a fifth invention).

In other words, if the overall center-of-gravity exists at the rear side of the bipedal walking body in the longitudinal direction with respect to the ankle joint of the leg in contact with the ground, then the leg is normally in contact with the ground at the heel of the foot portion thereof, and the contact location is substantially directly below the ankle joint of the leg. Therefore, in this case, the position in the horizontal plane (the position in the longitudinal direction and the lateral direction) of the ankle joint of the leg can be estimated as the position in the horizontal plane (the position in the longitudinal direction and the lateral direction) of the acting point of the floor reaction force acting on the leg. If the overall center-of-gravity exists at the front side of the bipedal walking body in the longitudinal direction with respect to the metatarsophalangeal joint of the foot portion of the leg in contact with the ground, then the leg is normally in contact with the ground at a toe of the foot portion thereof and the contact location is substantially directly below the metatarsophalangeal joint of the foot portion of the leg. Therefore, in this case, the position in the horizontal plane (the position in the longitudinal direction and the lateral direction) of the metatarsophalangeal joint of the foot portion of the leg can be estimated as the position in the horizontal plane (the position in the longitudinal direction and the lateral direction) of the acting point of the floor reaction force acting on the leg. If the overall center-of-gravity exists at the front side of the bipedal walking body in the longitudinal direction with respect to the ankle joint of the leg in contact with the ground and exists at the rear side with respect to the metatarsophalangeal joint of the foot portion of the leg, then the position of the acting point of the floor reaction force in the longitudinal direction substantially coincides with the position of the overall center-of-gravity in the longitudinal direction. The foot portion can be regarded as a rigid body that approximately extends from an ankle joint to a metatarsophalangeal joint, so that the acting point of a floor reaction force can be considered to exist on a segment obtained by projecting a segment that connects the ankle joint and the metatarsophalangeal joint onto a floor surface. In this case, therefore, the position in the horizontal plane (the position in the longitudinal direction and the lateral direction) of the point at which the overall center-of-gravity and the longitudinal position agree on a segment that connects the ankle joint and the metatarsophalangeal joint of a leg can be estimated as the position in the horizontal plane (the position in the longitudinal direction and the lateral direction) of the acting point of the floor reaction force acting on the leg.

Further, in the fourth or the fifth invention, the fourth step estimates the vertical position of the acting point of a floor reaction force acting on a leg in contact with the ground as the position away downward in the vertical direction by a predetermined value, which has been specified beforehand, from the vertical position of the ankle joint of the leg grasped in the tenth step (a sixth invention). In other words, the ankle joint of the leg in contact with the ground during walking or the like of the bipedal walking body is generally located at a constant height from a floor surface. Hence, the position away downward in the vertical direction by a predetermined value which has been set beforehand (a predetermined value corresponding to the constant height) from the vertical position of the ankle joint of the leg can be estimated as the vertical position of the acting point of a floor reaction force.

The height of the ankle joint of the leg in contact with the ground is generally constant. If only a portion adjacent to the toe side of a bottom surface of a foot portion of a leg is in contact with the ground when the bipedal walking body is moving, then the height of the ankle joint of the leg from a floor surface will be slightly greater than in a case where substantially the entire sole of the foot portion or a portion adjacent to the heel is in contact with the ground. Hence, in order to further improve the accuracy of estimating the vertical position of the acting point of a floor reaction force, the following is preferably performed in the sixth invention.

Whether each of a portion adjacent to a toe side and a portion adjacent to a heel side of a foot portion of the leg, which has been determined to be in contact with the ground, is in contact with the ground is determined in the ninth step, the vertical position of the ankle joint of the leg in contact with the ground and the vertical position of the metatarsophalangeal joint of the foot portion of the leg are grasped in the tenth step, and the fourth step estimates the vertical position of the acting point of the floor reaction force by using a vertical distance between the ankle joint and the metatarsophalangeal joint determined from the vertical position of the ankle joint and the vertical position of the metatarsophalangeal joint, which have been grasped in the tenth step, in place of the predetermined value if it is determined in the ninth step that only the portion adjacent to the toe side out of the portion adjacent to the toe side and the portion adjacent to the heel side of the foot portion is in contact with the ground (a seventh invention).

With this arrangement, in a state wherein only the portion adjacent to the toe side of the foot portion of the leg in contact with the ground is in contact with the ground, the position vertically away downward from the vertical position of the ankle joint of the leg by the vertical distance between the ankle joint and the metatarsophalangeal joint is estimated as the vertical position of the acting point of a floor reaction force. As a result, the accuracy of estimating the vertical position of the acting point of the floor reaction force can be enhanced.

BEST MODE FOR CARRYING OUT THE INVENTION

Figure 1:
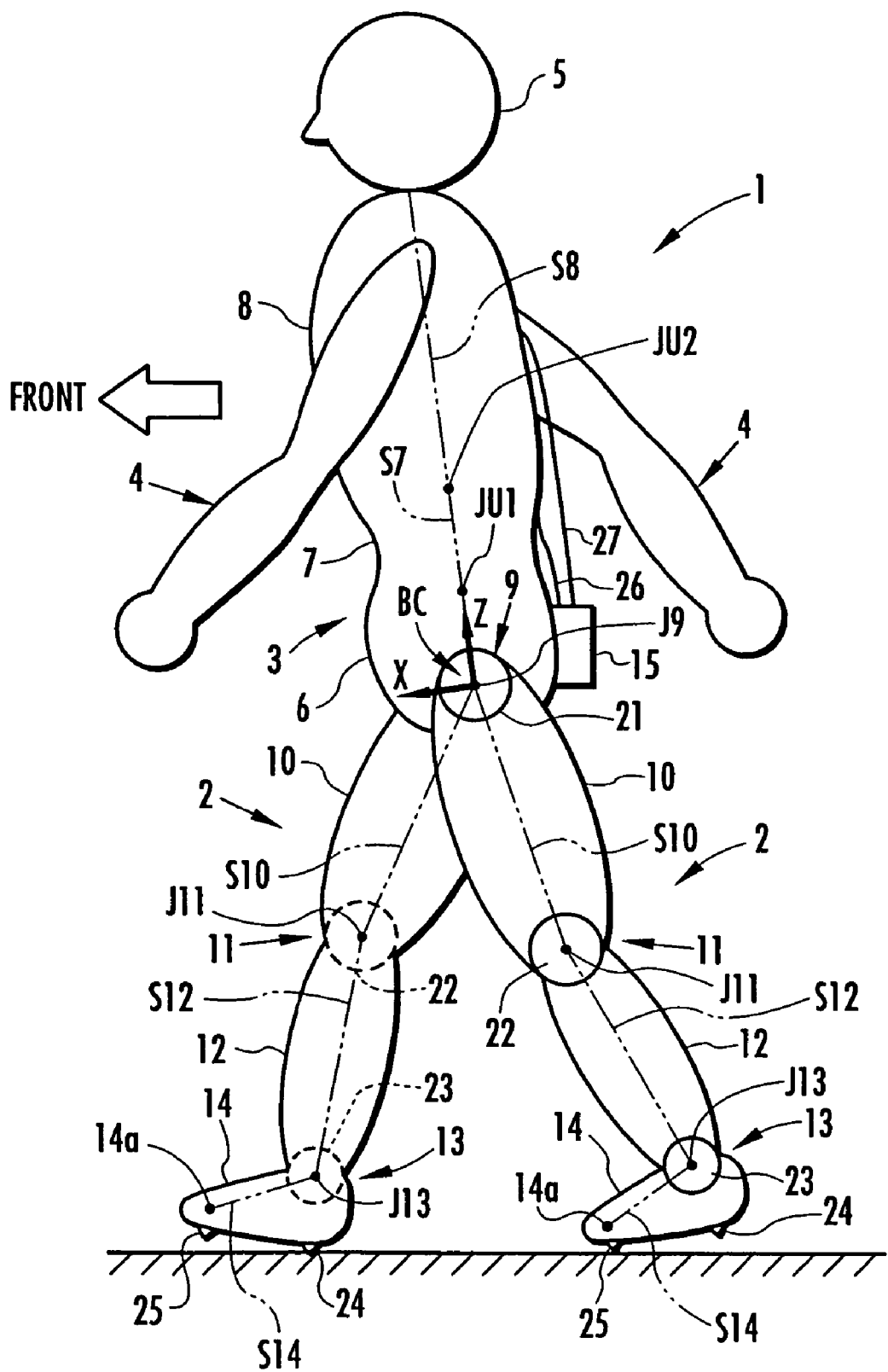
FIG. 1 is a diagram schematically showing an overall apparatus construction in an embodiment in which the present invention has been applied to a human being as a bipedal walking body.
Figure 2:
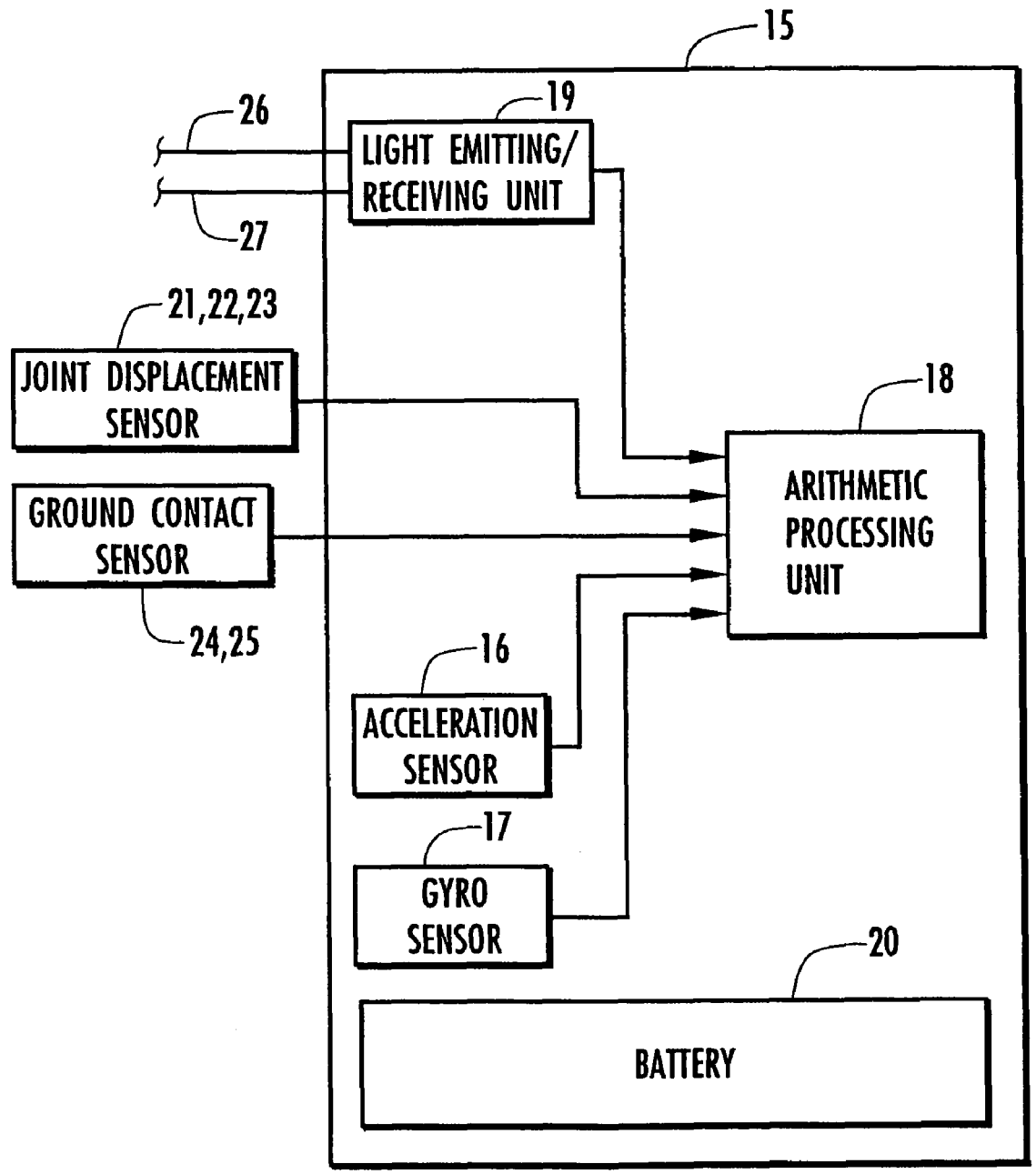
FIG. 2 is a block diagram showing the construction of a sensor box installed on the apparatus shown in FIG. 1.

An embodiment of the present invention will be explained with reference to FIG. 1 to FIG. 14. FIG. 1 is a diagram schematically showing an overall apparatus construction in an embodiment in which the present invention has been applied to a human being as a bipedal walking body. As shown in the figure, the construction of a human being 1 is roughly divided into a pair of right and left legs 2, 2, a body 3, a pair of right and left arms 4, 4, and a head 5. The body 3 is constructed of a waist 6, an abdomen 7, and a chest 8, and the waist 6 is connected to the legs 2 and 2, respectively, through the intermediary of a pair of right and left hip joints 9, 9. Further, the arms 4 and 4 extend from both right and left sides of the chest 8 of the body 3, and the head 5 is supported on the top end of the chest 8. Each leg 2 is provided with a thigh 10 extending from a hip joint 9, a crus 12 extending from the distal end of the thigh 10 through the intermediary of a knee joint 11, and a foot 14 extending from the distal end of the crus 12 through the intermediary of an ankle joint 13.

In the present embodiment, in order to estimate joint moments acting on the joints 9, 11, and 13 of the legs 2 of the human being 1 having the construction described above, the following apparatus is provided in the human being 1. A sensor box 15 is attached to the rear surface of the waist 6 through a member, such as a belt, which is not shown. The sensor box 15 houses an acceleration sensor 16 for detecting accelerations in 3-axis directions (translational accelerations), a gyro sensor 17 for detecting angular velocities in 3-axis directions (about 3 axes), an arithmetic processing unit 18 constructed using a microcomputer, a light emitter/receiver 19 for emitting light to be introduced into optical fibers 26 and 27, which will be discussed hereinafter, and receiving return light, and a battery 20 as a power source of the electronic units, such as the arithmetic processing unit 18, as shown in the block diagram of FIG. 2. The acceleration sensor 16 and the gyro sensor 17 are secured to the waist 6 through the intermediary of the sensor box 15 so as to move integrally with the waist 6.

Figure 3:
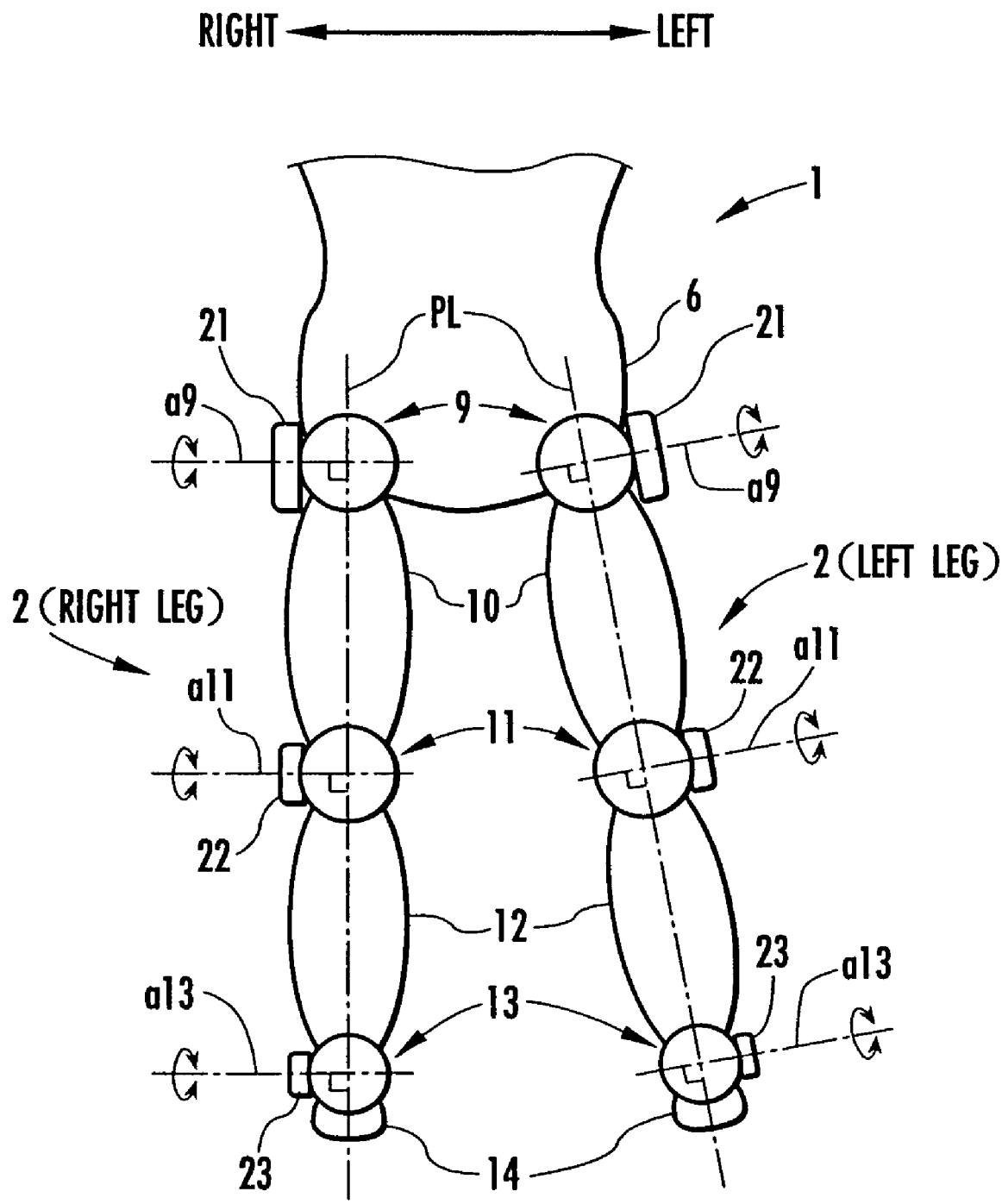
FIG. 3 is a diagram showing a relationship between the rotational angles of joints detected by joint displacement sensors installed on the apparatus shown in FIG. 1 and leg planes (a front view of the lower body of the human being)

The hip joint 9, the knee joint 11, and the ankle joint 13 of each leg 2 are provided with joint displacement sensors 21, 22 and 23 for detecting the displacement amounts of the respective joints through the intermediary of a member, such as a belt, which is not shown. A displacement amount detected by the joint displacement sensor 21 of the hip joint 9 is a rotational angle about three axes of the hip joint 9 (a three-dimensional amount composed of a set of rotational angles about these three axes), a displacement amount detected by the joint displacement sensor 22 of the knee joint 11 is a rotational angle about one axis of the knee joint 11, and a displacement amount detected by the joint displacement sensor 22 of the ankle joint 13 is a rotational angle about one axis of the ankle joint 13. In this case, one of the rotational angles detected by the joint displacement sensors 21 and the axes of rotation of the rotational angles detected by the joint displacement sensors 22 and 23 are axes a9, a11, and a13 that are substantially perpendicular to a leg plane PL as the plane passing substantially the centers of the hip joint 9, the knee joint 11, and the ankle joint 13, respectively, of a leg 2 to which the sensors are attached, as shown in FIG. 3. FIG. 3 is a diagram of the lower body of the human being 1 observed from the front side, the joint displacement sensors 21 to 23 being attached to each leg 2. In FIG. 3, the leg plane PL is a plane perpendicular to the paper surface of the drawing.

Here, the leg plane LP is a plane wherein the central points of the hip joint 9, the knee joint 11, and the ankle joint 13 of a leg 2 exist when the corresponding leg 2 is bent at the knee joint 11 to bend the leg 2. In other words, the leg 2 is bent in a state wherein the central points of the joints 9, 11, and 13 are positioned substantially on the leg plane PL. Further, for example, in the case of the left leg 2 shown in FIG. 3, if the left leg 2 is subjected to abduction by a motion of the hip joint 9, the leg plane PL corresponding to the left leg 2 inclines. The joint displacement sensors 21 to 23 detect the rotational angles about the aforesaid axes of rotation a9, a11, and a13 of the joints 9, 11, and 13, respectively, by, for example, a potentiometer or a rotary encoder.

Rotational angles about two axes detected by the joint displacement sensor 21 of the hip joint 9 will be explained with reference to FIG. 4. In the present embodiment, as shown in the figure, the joint displacement sensor 21 is connected to the sensor box 15 through the intermediary of an elastic member 50 shaped like a flat plate formed of rubber or the like. The end of the elastic member 50 adjacent to the sensor box 15 is connected to the sensor box 15 through the intermediary of a hard rigid member 50a extended from the sensor box 15. And the joint displacement sensor 21 detects, for example, the rotational angle of the hip joint 9 about an axis of rotation b9 in the direction in which the elastic member 50 extends (the rotational angle in the direction in which the elastic member 50 is twisted) and the rotational angle of the hip joint 9 about an axis of rotation c9 orthogonal to the axis of rotation b9 (the rotational angle in which the elastic member 50 is flexed) by using a distortion sensor, not shown, for detecting displacement amounts of the elastic member 50, or an optical fiber to be discussed later. The aforesaid axes of rotation b9 and c9 are parallel to the leg plane PL.

Returning to FIG. 1, two ground contact sensors 24 and 25 are provided on the soles of the foot portions 14 of the legs 2 (specifically, on the bottom surfaces of the shoes attached to the foot portions 14). Of the ground contact sensors 24 and 25, the ground contact sensor 24 is provided at the location directly below the ankle joint 13 (heel) and the ground contact sensor 25 is provided at the location directly below a metatarsophalangeal joint 14a of the foot 14 (the joint of the root of the thumb of the foot 14) (toe). These ground contact sensors 24 and 25 are sensors that output ON/OFF signals indicating whether the locations where they are installed are in contact with the ground. The detection outputs of the joint displacement sensors 21, 22 and 23, and the ground contact sensors 24 and 25 are supplied to the arithmetic processing unit 18 of the sensor box 15 through signal lines (not shown).

Further, as shown in FIG. 1, the two optical fibers 26 and 27 are extendedly provided from the sensor box 15 upward along the rear surface of the body 3, and the distal ends thereof are fixed to the rear surface of the abdomen 7 and the rear surface of the chest 8, respectively, through the intermediary of a member, such as belts, which are not shown. The optical fibers 26 and 27 are constituents of a detecting means for detecting the inclination angles (inclination angles on sagittal planes) of the abdomen 7 and the chest 8, respectively, relative to the waist 6. The measurement of the inclination angles of the abdomen 7 and the chest 8 by using these optical fibers 26 and 27 is accomplished by the following technique. The technique for measuring the inclination angle of the abdomen 7 by using the optical fiber 26 will be taken as an example and representatively explained. Light of a predetermined intensity is introduced into the optical fiber 26 from the light emitter/receiver 19 provided in the sensor box 15 (shown in FIG. 2), and the introduced light is reflected at the distal end of the optical fiber 26 to be back into the sensor box 15. The quantity of the returned light (the intensity of the returned light) is detected by the light emitter/receiver 19. Furthermore, the optical fiber 26 is provided with a plurality of notches (not shown) that admits slight leakage of light arranged in the lengthwise direction with intervals provided among them. Of the light introduced into the optical fiber 26, the light in the amount corresponding to the inclination angle of the abdomen 7 relative to the waist 6 leaks out of the optical fiber 26 through the notches. Thus, the return amount of the light back into the sensor box 15 corresponds to the inclination angle of the abdomen 7, so that the inclination angle of the abdomen 7 relative to the waist 6 is measured by detecting the return amount. In other words, a detection output of the light emitter/receiver 19 based on the return amount of light of the optical fiber 25 corresponds to the inclination angle of the abdomen 7 relative to the waist 6, and it is supplied to the arithmetic processing unit 18 as a signal indicating the inclination angle. The same applies to the technique for measuring an inclination angle of the chest 8 by using the optical fiber 27.

The rotational angles of the hip joints 9, the knee joints 11, and the ankle joints 13 detected by the joint displacement sensors 21, 22, and 23, respectively, are the rotational angles whose reference (zero point) is defined as the state wherein the human being 1 stands in an upright posture with both foot portions 14 and 14 oriented forward in parallel (hereinafter referred to as the reference posture state of the human being 1). The same applies to the inclination angles of the abdomen 7 and the chest 8 detected by the optical fibers 26 and 27.

Figure 5:
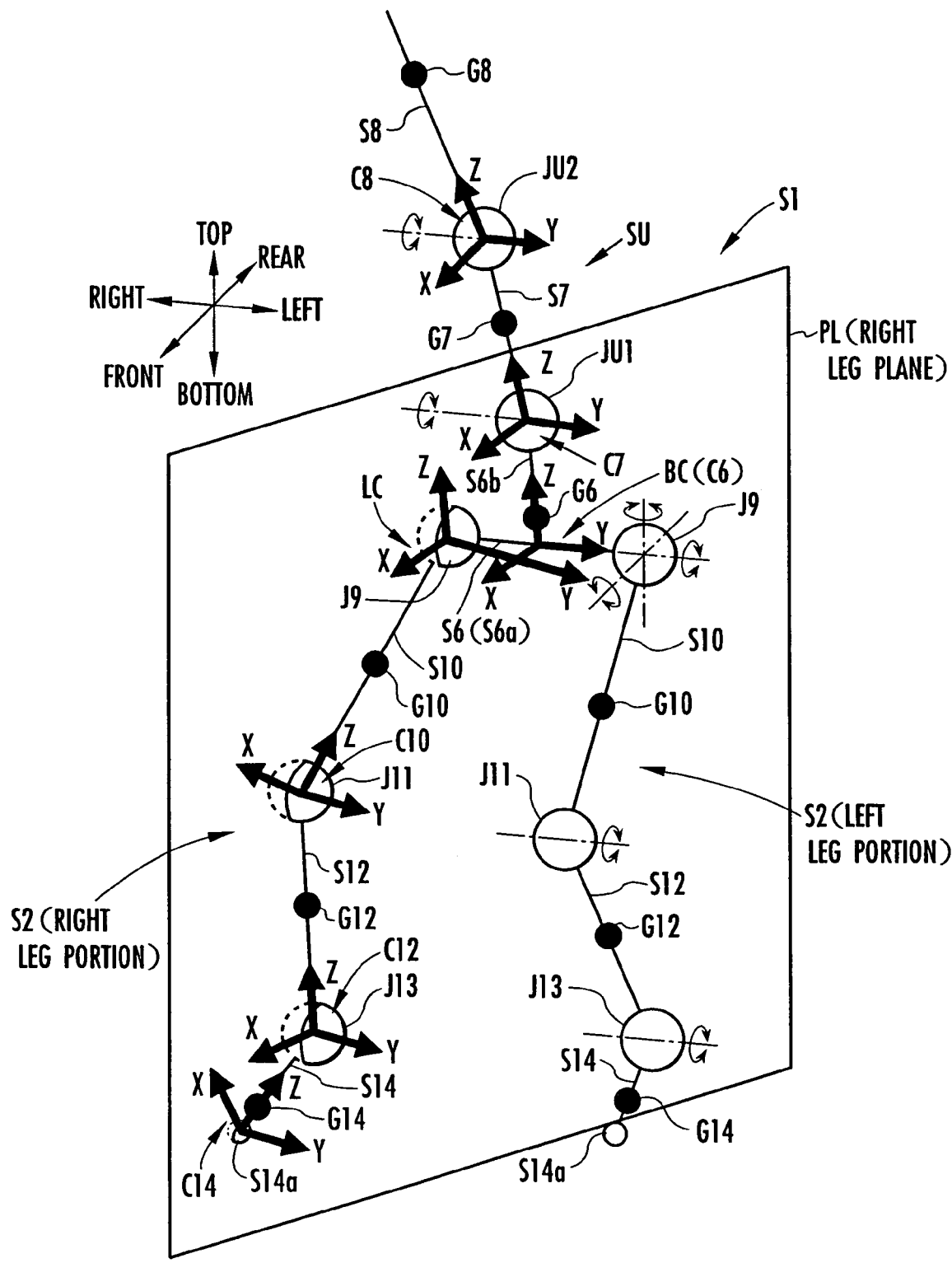
FIG. 5 is a perspective view showing a rigid link model and a leg plane used in the embodiment.

Here, the rigid link model of the human being 1 and the coordinate system used in the present embodiment will be explained. FIG. 5 shows the rigid link model S1 and the coordinate system. The rigid link model S1 is shown also in FIG. 1 by virtual lines. In the present embodiment, the rigid link model S1 expresses the human being 1 in the form of a link assembly composed of nine rigid elements and eight joint elements. To be more specific, the rigid link model S1 is roughly divided into a pair of leg portions S2, S2 respectively corresponding to the legs 2 of the human being 1, and the upper body SU corresponding to the body (the portion above the waist 6) of the human being 1. The upper body SU is constructed as a link assembly formed by connecting a rigid element S6 corresponding to the waist 6 of the human being 1 and a rigid element S7 corresponding to the abdomen 7 by a joint element JU1, and by further connecting the rigid element S7 and a rigid element S8 corresponding to the chest 8 by a joint element JU2. Hereinafter, the rigid elements S6, S7, and S8 will be referred to as the waist element S6, the abdomen element S7, the chest element S8, and the joint elements JU1 and JU2 will be referred to as the upper body lower joint JU1 and the upper body upper joint JU2 in some cases.

In this case, the waist element S6 shaped like an inverted T has the upper body lower joint JU1 provided on the upper end thereof and also has a pair of joint elements J9, J9 (hereinafter referred to simply as hip joints J9 in some cases) corresponding to a pair of hip joints 9, 9 of the human being 1, which are provided on both ends, the right and left ends, thereof. In other words, the waist element S6 is formed of a part S6a that extends between the hip joints J9, J9 in the direction (lateral direction) of a segment connecting the centers thereof and a part S6b that extends substantially upward toward the upper body lower joint JU1 from the middle of the part S6a. Here, the upper body lower joint JU1 corresponds to a joint assumed to be on the spine of the human being 1 in the vicinity of the boundary between the waist 6 and the abdomen 7 of the human being 1. The upper body upper joint JU2 corresponds to a joint assumed to be on the spine of the human being 1 in the vicinity of the boundary between the abdomen 7 and the chest 8. The actual spine controlling the bending operation of the body 3 of the human being 1 is formed of many joints, while the bending operation of the upper body SU in the rigid link model S1 is accomplished by the two joint elements, namely, the upper body lower joint JU1 and the upper body upper joint JU2. Further, the abdomen element S7 extends between the upper body lower joint JU1 and the upper body upper joint JU2 in the direction of a segment connecting the centers thereof. As shown in FIG. 1, the chest element S8 is supposed to extend from the upper body upper joint JU2 to the root of the neck of the human being 1 (more specifically, a region on the spine in the vicinity of the boundary between the body 3 and the neck).

Each leg portion S2 of the rigid link model S1 is constructed as a link assembly formed by connecting a rigid element S10 corresponding to the thigh 10 to the waist element S6 through the intermediary of the hip joint J9, connecting a rigid element S12 corresponding to the crus 12 through the intermediary of a joint element J11 corresponding to the knee joint 11, and connecting a rigid element S14 corresponding to the foot 14 through the intermediary of a joint element J13 corresponding to the ankle joint 13. Hereinafter, the rigid elements S10, S12, and S14 will be referred to as the thigh element S10, the crus element S12, and the foot element S14, and the joint elements J11 and J13 will be referred to simply as the knee joint J11 and the ankle joint J13 in some cases.

In this case, the thigh element S10 and the crus element S12 extend between the joint elements at both ends thereof, respectively, in the direction of the segment connecting the centers thereof. Regarding the foot element S14, the leading end of the foot element S14 corresponds to the metatarsophalangeal joint 14a (hereinafter referred to as the MP joint 14a) of the foot 14 of the human being 1, and the foot element S14 extends from the ankle joint 13 (J13) to the metatarsophalangeal joint 14a (hereinafter referred to as the MP joint 14a) of the foot 14, as shown in FIG. 1. In the rigid link model S1, the leading end of the foot element S14 does not have the function as a joint; however, for the sake of convenience, the leading end will be referred to as the MP joint J14a in some cases hereinafter.

The rigid elements and the joint elements of the rigid link model S1 constructed as described above are capable of performing motions such that their mutual positional relationship and posture relationship (orientation relationship) will be substantially identical to the mutual positional relationship and posture relationship of the parts of the human being 1 corresponding to the rigid elements and the joint elements by the rotational motions of the joint elements. In this case, each of the upper body lower joint JU1 and the upper body upper joint JU2 is capable of rotations about three axes, one axis among them being used as a measurement axis to measure rotations about the measurement axis (arrows shown in association with the joint elements JU1 and JU2 in FIG. 5 (arrows indicating the directions of rotation)). The measurement axis is an axis parallel to the segment connecting the centers of the aforesaid pair of hip joints J9 and J9 (the direction in which a portion S6a of the waist element S6 extends) in the present embodiment. The hip joint J9 of each leg portion S2 is capable of rotation about three axes, as indicated by the arrows (arrows indicating the directions of rotation) representatively shown in FIG. 5 in relation to the hip joint J9 of the leg portion S2 on the left side. Further, the knee joint J11 and the ankle joint J13 of each leg portion S2 are capable of rotation about one axis, as indicated by the arrows (arrows indicating the directions of rotation) representatively shown in FIG. 5 in relation to the joint elements J11 and J13 of the leg portion S2 on the left side. The axes of rotation of the knee joint J11 and the ankle joint J13, respectively, are axes perpendicular to a leg plane (the one for the leg portion S2 on the left side being not shown in FIG. 5) that passes the centers of the hip joint J9, the knee joint J11, and the ankle joint J13, respectively. The rotational operations of the hip joint J9, the knee joint J11, and the ankle joint J13 of the leg portion S2 on the right side are the same as those of the leg portion S2 on the left side. In this case, the axis of rotation (one axis) of each of the knee joint J11 and the ankle joint J13 of the leg portion S2 on the right side is an axis perpendicular to the leg plane PL shown in association with the leg portion S2 on the right side. Incidentally, each of the hip joints J9 is capable of rotations about the three axes in either leg portion S2, so that it is also capable of rotations about an axis perpendicular to a leg plane associated with each leg portion S2.

Further, in the rigid link model S1, the weight and the length (the length in the axial direction) of each rigid element and the position of the center-of-gravity of each rigid element (the position in each rigid element) are specified beforehand and stored and retained in a memory, not shown, of the arithmetic processing unit 18. Black dots G8, G7, G6, G10, G12, and G14 shown in FIG. 5 illustratively indicate the centers of gravity of the chest element S8, the abdomen element S7, the waist element S6, the thigh element S10, the crus element S12, and the foot element S14, respectively. The waist element S6 is shaped like an inverted T, as mentioned above, so that the length thereof is divided into the length of the portion S6a and the portion S6b mentioned above.

The weight, the length, and the position of the center-of-gravity of each rigid element are basically set to be substantially the same as the weight, the length, and the position of the center-of-gravity of the corresponding rigid body of the human being 1 associated with each rigid element. For example, the weight, the length, and the position of the center-of-gravity of the thigh element S10 are substantially the same as the actual weight, length, and position of the center-of-gravity of the thigh 10 of the human being 1. It should be noted that the weight and the position of the center-of-gravity are the weight and the position of the center-of-gravity in a state in which the human being 1 is provided with the apparatus of the present embodiment. Further, the weight and the position of the center-of-gravity of the chest element S8 are the weight and the position of the center-of-gravity obtained by adding up the chest 8, both arms 4, 4, and the head 5 of the human being 1. Supplementally, the positional changes in the center-of-gravity of the chest element S8 caused by motions of both arms 4, 4 (an operation for swinging the arms forward and backward) when the human being 1 moves are relatively small and the position of the center-of-gravity is maintained substantially at a fixed position of the chest element S8. Further, the position of the center-of-gravity of each rigid element is set as a position vector in an element coordinate system to be discussed later, which is fixedly set beforehand on each rigid element, and set in terms of a coordinate component value of the element coordinate system.

The weight, the length, and the position of the center-of-gravity of each rigid element may be basically set on the basis of actually measured values of the dimension and weight of each part of the human being 1; alternatively, however, they may be estimated from the height and the weight of the human being 1 on the basis of average statistical data of human beings. In general, the position of the center-of-gravity, the weight, and the length of the corresponding rigid bodies of the human being 1 that are associated with the rigid elements are correlated with the height and weight (total weight) of a human being, and it is possible to estimate the position of the center-of-gravity, the weight, and the length of the corresponding rigid bodies of the human being 1 corresponding to the rigid elements with relatively high accuracy from the actual measurement data of the height and the weight of the human being 1 on the basis of the correlation.

Incidentally, in FIG. 5, the centers of gravity G8, G7, G6, G10, G12, and G14 are shown such that they are positioned on the axial centers of the rigid elements respectively corresponding thereto for the sake of convenience; however, they are not necessarily positioned on the axial centers, and may exist at positions deviated from the axial centers.

In the present embodiment, for the rigid link model S1, the following coordinate system is set in advance. Specifically, as shown in FIG. 5, a body coordinate system BC is fixedly set to the waist element S6. The body coordinate system BC is set as a three-dimensional coordinate system (XYZ coordinate system) in which the midpoint of the segment connecting the centers of the pair of hip joints J11 and J11 (the central point of the portion S6a of the waist element S6) is defined as its origin, the axis in the direction of the segment is defined as Y axis, the axis in the direction toward the center of the upper body lower joint JU1 from the origin is defined as Z axis, and the axis in the direction orthogonal to these Y axis and Z axis is defined as X axis. In the aforesaid reference posture state of the human being 1, the X axis, the Y axis, and the Z axis of the body coordinate system BC are oriented in the longitudinal direction, the lateral direction, and the up-down direction (vertical direction), respectively, of the human being 1, and an XY plane is a horizontal plane. In the present embodiment, the origin of the body coordinate system BC corresponds to a reference point in the present invention.

The leg plane PL for each of the legs 2 has a leg coordinate system LC fixed and set. In FIG. 5, for the sake of convenience, only the leg coordinate system LC corresponding to the leg plane PL of the leg portion S2 on the right side is representatively shown. The leg coordinate system LC is a three-dimensional coordinate system (XYZ coordinate system) in which the midpoint of the hip joint J9 on the leg plane PL is defined as its origin, the axis in the direction perpendicular to the leg plane PL is defined as Y axis, the axis in the direction parallel to the axis obtained by projecting the Z axis of the body coordinate system BC onto the leg plane PL is defined as Z axis, and the axis in the direction orthogonal to these Y axis and Z axis is defined as X axis. Incidentally, the XZ plane of the leg coordinate system LC agrees with the leg plane PL.

Further, element coordinate systems denoted by, for example, reference symbols C8, C7, C6, C10, C12, and C14, are fixedly set on the rigid elements. In the present embodiment, the element coordinate system C6 of the waist element S6 is set to be identical to the body coordinate system BC. The element coordinate systems C8, C7, C10, C12, and C14 of the chest element S8, the abdomen element S7, the thigh element S10, the crus element S12, and the foot element S14, respectively, are set to be three-dimensional coordinate systems (XYZ coordinate systems) in which the central points of the upper body upper joint JU2, the upper body lower joint JU1, the knee joint J11, the ankle joint J13, and the MP joint J14a, respectively, are defined as the origins. In other words, in the element coordinate systems C10, C12, and C14 of the rigid elements S10, S12, and S14 of each leg portion S2, the central points of the joint elements on the farther side from the waist element S6 among the joint elements on both ends of each of the rigid elements S10, S12, and S14 are defined as the origins. Further, in the element coordinate systems C7 and C8 of the abdomen element S7 and the chest element S8 of the upper body SU, the central points of the joint elements closer to the waist element S6 among the joint elements on both ends of each of the abdomen element S7 and the chest element S8 are defined as the origins. FIG. 3 shows the element coordinate systems C10, C12, and C14 of only the leg portion S2 on the right side for the sake of convenience; however, element coordinate systems similar to those of the leg portion S2 on the right side are also set for the leg portion S2 on the left side.

Further, the element coordinate systems C8 and C7 have the Z axes thereof set in the direction in which the chest element S8 and the abdomen element S7, respectively, extend (the axial direction), and the Y axes thereof set in the same direction as that of the Y axis of the body coordinate system BC. Further, the element coordinate systems C10, C12, and C14 have the Z axes thereof set in the direction in which the thigh element S10, the crus element S12, and the foot element S14, respectively, extend (the axial direction), and the Y axes thereof set in the direction of the normal line of the leg plane PL (the direction parallel to the Y axis of the leg coordinate system LC). In any one of the element coordinate systems C8, C7, C10, C12, and C14, the X axes are set in the direction orthogonal to the Y axes and the Z axes. In the following explanation, the element coordinate systems C8, C7, C6, C10, C12, and C14 will be referred to as the chest coordinate system C8, the abdomen coordinate system C7, the waist coordinate system C6, the thigh coordinate system C10, the crus coordinate system C12, and the foot coordinate system C14, respectively, in some cases.

The element coordinate systems C8, C7, C10, C12, and C14 do not have to be always set as described above; basically, the origins and the directions of the axes thereof may be arbitrarily set.

Figure 6:
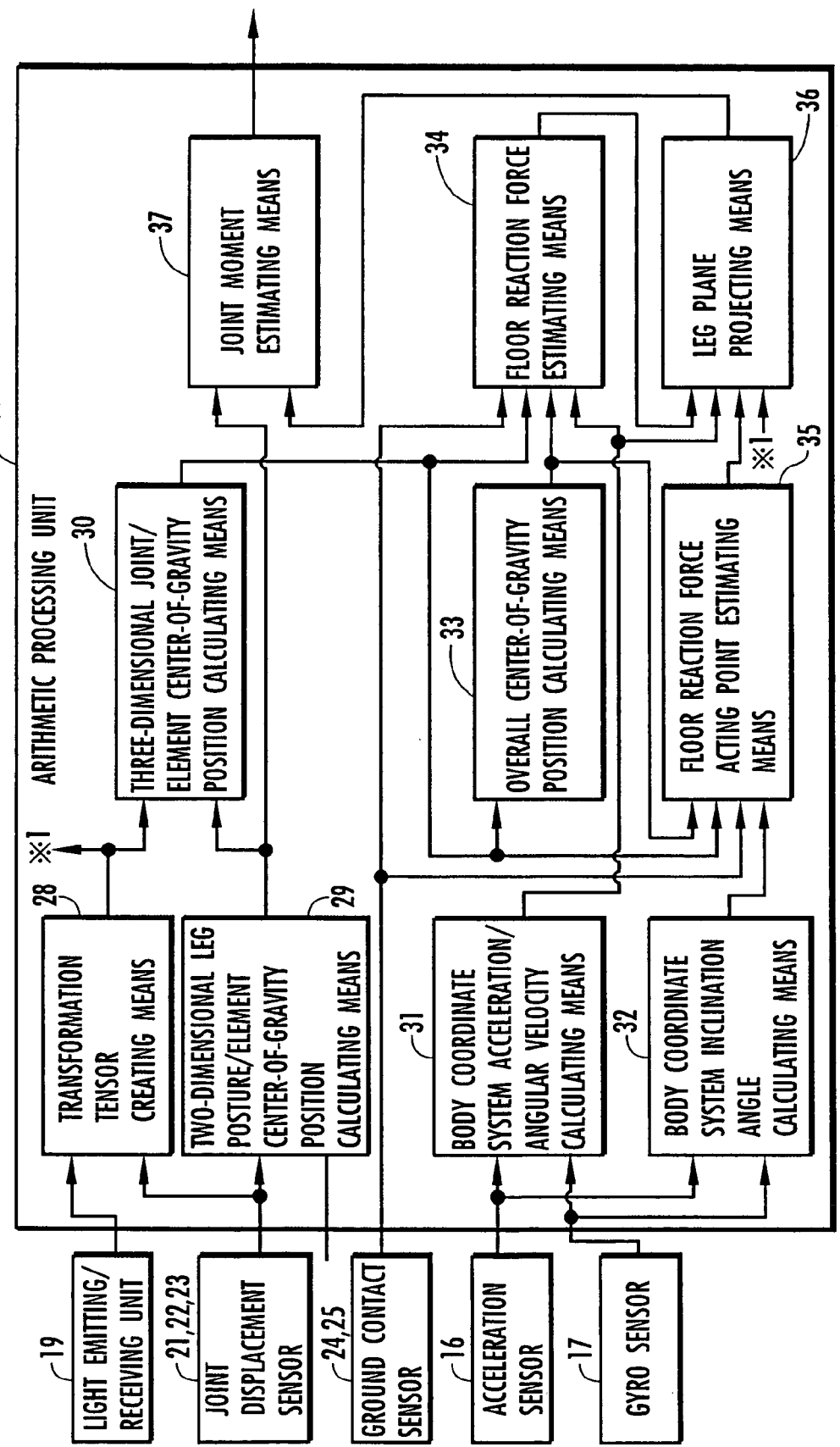
FIG. 6 is a block diagram showing a functional means of an arithmetic processing device shown in FIG. 2.

FIG. 6 is a block diagram showing the arithmetic processing function of the arithmetic processing unit 18. As shown in the figure, the arithmetic processing unit 18 is provided with a transformation tensor creating means 28 for creating transformation tensors for carrying out coordinate conversion, which will be discussed later, on the basis of detection outputs of the joint displacement sensors 21 of the hip joints 9 and the light emitter/receiver 19, a two-dimensional leg posture/element center-of-gravity position calculating means 29 for determining the position of each joint element on the leg plane PL of each leg 2 of the rigid link model S1 and the posture (inclination angle) of each rigid element and the position of the center-of-gravity of each rigid element on the basis of detection outputs of the joint displacement sensors 21, 22, and 23, a three-dimensional joint/element center-of-gravity position calculating means 30 for determining the values of three-dimensional position vectors (coordinate component values) of the centers of gravity of the joint elements and the rigid elements of the rigid link model S1 in the body coordinate system BC by using the transformation tensor created by the transformation tensor creating means 28 and the positions/postures determined by the two-dimensional leg posture/element center-of-gravity position calculating means 29, a body coordinate system acceleration/angular velocity calculating means 31 for determining the values of the acceleration vector (translational acceleration) of the origin of the body coordinate system BC and the angular velocity vector (coordinate component values in the body coordinate system BC) on the basis of detection outputs of the acceleration sensor 16 and the gyro sensor 17, and a body coordinate system inclination angle calculating means 32 for calculating inclination angles relative to the vertical direction of the body coordinate system BC on the basis of detection outputs of the acceleration sensor 16 and the gyro sensor 17.

The arithmetic processing apparatus 18 is further provided with an overall center-of-gravity position calculating means 33 for determining the value of the position vector of the overall center-of-gravity of the rigid link model S1 (the overall center-of-gravity of the human being 1) in the body coordinate system BC by using the value of the position vector of the center-of-gravity of each rigid element determined by the three-dimensional joint/element center-of-gravity position calculating means 29.

The arithmetic processing unit 18 is further provided with a floor reaction force estimating means 34 for estimating the value of a floor reaction force vector (translational floor reaction force) acting on the legs 2 and 2 of the human being 1 (the coordinate component value) in the body coordinate system BC by using the value of the position vector of each ankle joint J13 determined by the three-dimensional joint/element center-of-gravity position calculating means 30, the value of the position vector of the overall center-of-gravity determined by the overall center-of-gravity position calculating means 33, the value of the acceleration vector of the origin of the body coordinate system BC determined by the body coordinate system acceleration/angular velocity calculating means 31, and the detection outputs of the ground contact sensors 24 and 25, and a floor reaction force acting point estimating means 35 for estimating the value of the position vector of the acting point of a floor reaction force vector (hereinafter referred to simply as the floor reaction force acting point) acting on the legs 2 in the body coordinate system BC by using the values of the position vectors of each ankle joint J13 and each MP joint J14a determined by the three-dimensional joint/element center-of-gravity position calculating means 30, the inclination angle of the body coordinate system BC determined by the body coordinate system inclination angle calculating means 32, the value of the position vector of the overall center-of-gravity determined by the overall center-of-gravity position calculating means 33, and the detection outputs of the ground contact sensors 24 and 25.

And, the arithmetic processing unit 18 is provided with a leg plane projecting means 36 for projecting the value of the floor reaction force vector determined by the floor reaction force estimating means 34, the value of the position vector of the floor reaction force acting point determined by the floor reaction force acting point estimating means 35, and the values of the acceleration vector and the angular velocity vector determined by the body coordinate system acceleration/angular velocity calculating means 31 onto the leg plane PL associated with each leg 2 by using the transformation tensor created by the transformation tensor creating means 28, and a joint moment estimating means 37 for estimating a joint moment acting on the ankle joint 13, the knee joint 11, and the hip joint 9 of each leg 2 by using the values (two-dimensional values) obtained by the projection and the positions/postures determined by the two-dimensional leg posture/element center-of-gravity position calculating means 29.

The details will be given later, but the arithmetic processing unit 18 sequentially carries out the arithmetic processing of the aforesaid means 28 to 37 at a predetermined arithmetic processing cycle so as to sequentially calculate the estimated value of the joint moment lastly by the joint moment estimating means 37 in each arithmetic processing cycle.

The operation of the apparatus of the present embodiment will now be explained in combination with detailed arithmetic processing of each means of the arithmetic processing unit 18. In the following explanation, in general, the transformation tensor for coordinate-converting a vector quantity from a certain coordinate system Ca into another coordinate system Cb, namely, the tensor for converting a vector quantity expressed by a component value of the coordinate system Ca into a vector quantity expressed by a component value of the coordinate system Cb will be denoted as "R(Ca→Cb)." The position vector of a certain point P or a region P observed in a certain coordinate system Ca is denoted as U(P/Ca). Vector A of a physical amount, such as an acting force or acceleration of an object Q or a region Q, which is expressed in terms of a coordinate component value of a certain coordinate system Ca, will be denoted as A(Q/Ca) In this case, if the coordinate component values of the position vector U(P/Ca) or the physical amount vector A(Q/Ca) on the coordinate system Ca are to be expressed, then x, y, and z, which are the designations of coordinate axes, are further added to express them. For example, an X-coordinate component of the position vector U(P/Ca) is expressed as U(P/Ca)x.

The element coordinate systems C8, C7, C6, C10, C12, and C14 may be referred to as C_chest, C_abdomen, C_waist, C_thigh, C_crus, and C_foot, which use the designations of their corresponding parts. This applies also to the rigid elements S8, S7, S6, S10, S12, and S14 and to the centers of gravity G8, G7, G6, G10, G12, and G14 of the rigid elements S. For instance, the waist rigid element S8 and the center-of-gravity thereof G8 may be expressed as S_waist and G_waist, respectively. If it is necessary to distinguish between right and left of the thighs 10, the cruses 12, and the feet 14, then "right" and "left" are further added to describe them. For instance, the right thigh element S10 may be referred to as S_right thigh. Further, the hip joint J9, the knee joint J11, the ankle joint J13, and the MP joint J14a may be referred to as J_hip, J_knee, J_ankle, and J_MP, respectively. In this case also, if it is necessary to distinguish between right and left, then "right" and "left" are further added to describe them, as mentioned above.

The arithmetic processing unit 18 captures the detection outputs of the joint displacement sensors 21, 22 and 23, the light emitter/receiver 19, the acceleration sensor 16, and the gyro sensor 17 through the intermediary of an A/D converter, not shown, and also the detection outputs (ON/OFF signals) of the ground contact sensors 24 and 25 at a predetermined arithmetic processing cycle. Then, first, the arithmetic processing of the transformation tensor creating means 28, the two-dimensional leg posture/element center-of-gravity position calculating means 29, and the three-dimensional joint/element center-of-gravity position calculating means 30 is sequentially carried out.

The arithmetic processing of the transformation tensor creating means 28 creates a transformation tensor R(LC→BC) for accomplishing coordinate conversion of vector amounts between the leg coordinate system LC corresponding to each leg plane PL and the body coordinate system BC, and transformation tensors R(C_abdomen→BC) and R(C_chest→BC) for accomplishing coordinate conversion of vector amounts between each of the element coordinate system C7 of the abdomen element S7 and the element coordinate system C8 of the chest element S8 and the body coordinate system BC.

The transformation tensor R(LC→BC) is a tensor indicating the direction of a normal line vector of the leg plane PL observed in the body coordinate system BC. In the present embodiment, this transformation tensor R(LC→BC) is calculated according the following expression (1) by using rotational angles α and β about the aforesaid axes of rotation b9 and c9, respectively (refer to FIG. 4), detected by the joint displacement sensor 21 of the hip joint 9.

$$R(LC \to BC) = R(C\_b \to BC) \times R(LC \to C\_b) \quad (1)$$

where $$R(LC \to C\_b) = \begin{bmatrix} 1 & 0 & 0 \\ 0 & \cos\beta & -\sin\beta \\ 0 & \sin\beta & \cos\beta \end{bmatrix} \times \begin{bmatrix} \cos\alpha & -\sin\alpha & 0 \\ \sin\alpha & \cos\alpha & 0 \\ 0 & 0 & 1 \end{bmatrix}$$

Figure 4:
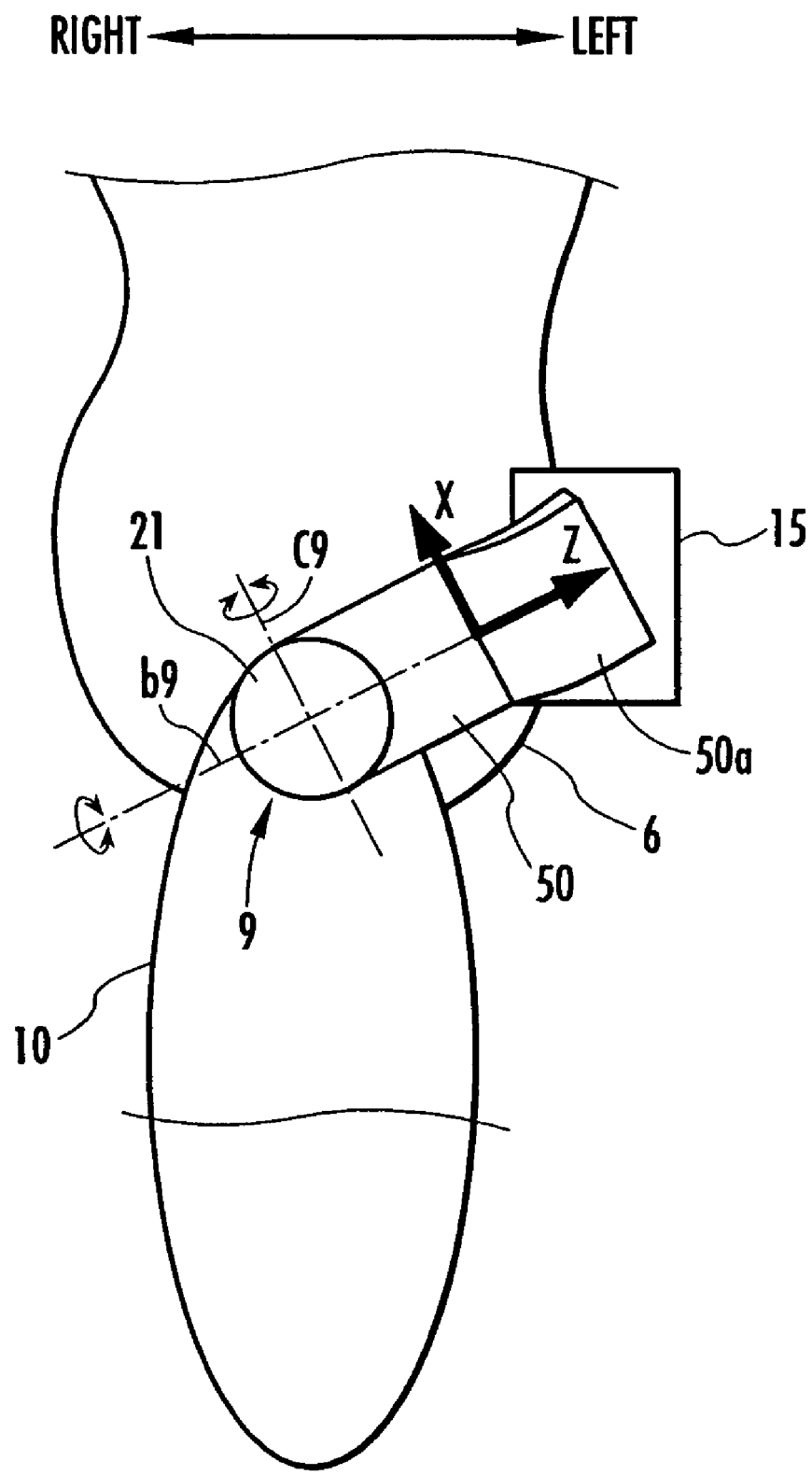
FIG. 4 is a diagram for explaining the detection of the rotational angle of a hip joint by a joint displacement sensor of a hip joint in the apparatus shown in FIG. 1 (a side view of a portion around the waist of the human being).

Here, C_b in expression (1) is a three-dimensional coordinate system that has an origin at one end of the elastic member 50 adjacent to the sensor box 15 (the one end secured to the rigid member 50a extended from the sensor box 15), the directions of the axes of rotation b9 and c9 being defined as the Z-axis direction and the X-axis direction, respectively, as shown in FIG. 4. The Y axis of this coordinate system C_b is in the direction perpendicular to the paper surface of FIG. 4 and the direction perpendicular to the leg plane PL in the aforesaid reference posture state of the human being 1. And, R(LC→C_b) of expression (1) denotes a tensor indicating the direction of the normal line vector of the leg plane PL observed in the coordinate system C_b. Further, R(C_b→BC) in expression (1) denotes a tensor for coordinate-converting a vector amount observed in the aforesaid coordinate system C_b into a vector amount observed in the body coordinate system BC. In this case, the coordinate system C_b is secured to the waist 6 through the intermediary of the rigid member 50a and the sensor box 15, so that it has fixed position/posture relationship with the body coordinate system BC. For this reason, the tensor R(C_b→BC) has a constant value (fixed value); it is set beforehand when the apparatus in accordance with the present embodiment is mounted on the human being 1, and stored and retained in a memory of the arithmetic processing unit 18. Thus, the transformation tensor R(LC→BC) is calculated according to the above expression (1) by using the rotational angles α and β about the aforesaid axes of rotation b9 and c9 detected by the joint displacement sensor 21 of the hip joint 9. The transformation tensor R(LC→BC) is determined on each of the right and left legs 2 separately.

The transformation tensors R(C_abdomen→BC) and R(C_chest→BC) are created as described below. First, on the basis of a detection output of the light emitter/receiver 19, the inclination angles of the abdomen element S7 and the chest element S8 relative to the waist element S6 of the rigid link model S1 (more specifically, the inclination angles on a sagittal plane (XZ plane) relative to the Z-axis direction of the body coordinate system BC) are grasped. Then, the transformation tensor R(C_abdomen→BC), for example, is expressed by a tertiary matrix as shown by expression (2) given below when the inclination angle of the abdomen 7 relative to the waist 6 is denoted by θy (where the inclination angle θy defines the direction of the inclination toward the front of the human being 1 as the positive direction).

$$R(C\_abdomen \to BC) = \begin{bmatrix} \cos\theta y & 0 & \sin\theta y \\ 0 & 1 & 0 \\ -\sin\theta y & 0 & \cos\theta y \end{bmatrix} \quad (2)$$

The same applies to the transformation tensor R(C_chest→BC). Supplementally, the present embodiment assumes that the upper body lower joint JU1 and the upper body upper joint JU2 of the rigid link model S1 are capable of rotation about one axis (about the Y axis of C_abdomen and C_chest), and measures the inclination angles of the abdomen element S7 and the chest element S8 relative to the waist element S6 produced by the rotation; hence, the transformation tensors R(C_abdomen→BC) and R(C_chest→BC) are expressed by the matrix of the form of the right side of the aforesaid expression (2). Alternatively, however, it may be assumed that the upper body lower joint JU1 and the upper body upper joint JU2 are respectively capable of rotation about, for example, two axes (e.g., two axes, namely, the Y axis and the X axis, of C_abdomen and C_chest), and the inclination angles of the abdomen element S7 and the chest element S8 about the two axes may be measured. In such a case, the transformation tensors R(C_abdomen→BC) and R(C_chest→BC) will take more complicated forms.

Transposing the transformation tensors R(LC→BC) and R(C_abdomen→BC), and R(C_chest→BC) provides the transformation tensors for accomplishing inverse transformation thereof. Thus, $R(BC \to LC) = R(LC \to BC)^T$, $R(BC \to C\_abdomen) = R(C\_abdomen \to BC)^T$, and $R(BC \to C\_chest) = R(C\_chest \to BC)^T$ (T meaning transposition).

The arithmetic processing of the aforesaid two-dimensional leg posture/element center-of-gravity position calculating means 29 first calculates inclination angles θ_thigh, θ_crus, and θ_foot of the thigh 10, the crus 12, and the foot 14, which are corresponding rigid bodies of a leg 2, as the inclination angles of the thigh element S10, the crus element S12, and the foot element S14 of the rigid link model S1, which respectively corresponding thereto, from the rotational angles about the axes perpendicular to the leg plane PL of the joints 9, 11, and 13, respectively (the axes of rotation a9, a11, and a13 in FIG. 3) grasped from the detection outputs of the joint displacement sensors 21 to 23 of the leg 2. Here, the inclination angles θ_thigh, θ_crus, and θ_foot denote the inclination angles relative to the Z-axis direction of the leg coordinate system LC related to the leg plane PL.

Figure 7:
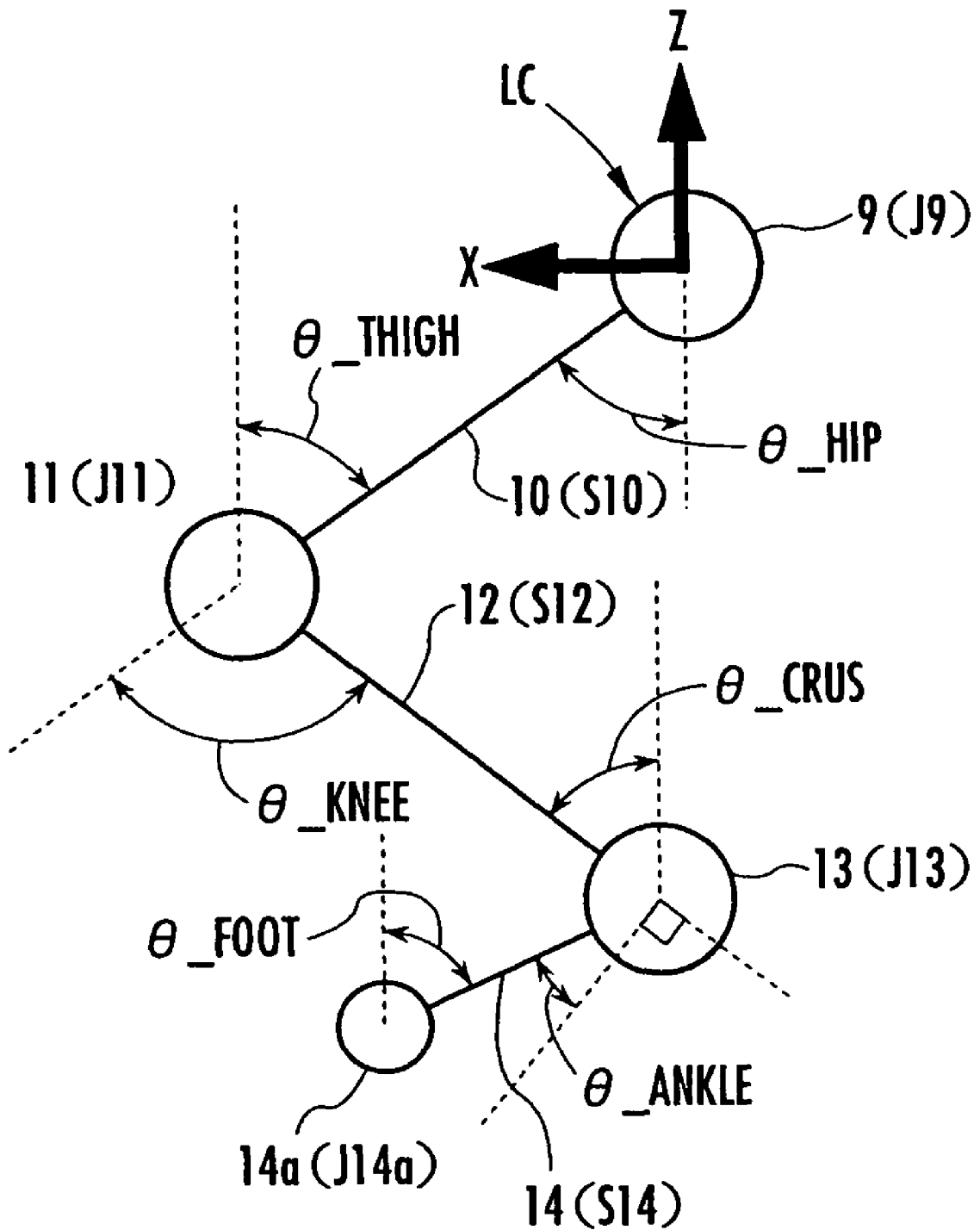
FIG. 7 is a diagram for explaining the processing for determining a posture of a leg by a means for calculating a two-dimensional leg posture and the position of the center-of-gravity of an element shown in FIG. 6.

Specifically, as shown in FIG. 7, if detected rotational angles of the hip joint 9, the knee joint 11, and the ankle joint 13 (the rotational angles about axes perpendicular to the leg plane PL (XZ plane of the leg coordinate LC) from the aforesaid reference posture state) are denoted as θ_hip, θ_knee, and θ_ankle, then θ_thigh, θ_crus, and θ_foot are sequentially determined according to the following expressions (3a) to (3c), respectively.

$$\theta\_thigh = -\theta\_hip \quad (3a)$$

$$\theta\_crus = \theta\_thigh + \theta\_knee \quad (3b)$$

$$\theta\_foot = \theta\_crus - \theta\_ankle + 90° \quad (3c)$$

In the example of FIG. 7, θ_hip>0, θ_knee>0, and θ_ankle>0, and θ_thigh<0, θ_crus>0, and θ_foot<0. Further, the calculation of θ_thigh, θ_crus, and θ_foot is carried out for each of the leg portions S2 separately.

Next, the positions of the joint elements of each leg portion S2 on the XZ plane of the leg coordinate system LC, that is, the leg plane PL, are determined by using the θ_thigh, θ_crus, and θ_foot determined as described above and the lengths of the rigid elements of each leg portion S2 stored and retained in the memory of the arithmetic processing unit 18 beforehand. Specifically, position vectors U(J_hip/LC), U(J_knee/LC), U(J_ankle/LC), and U(J_MP/LC) on the leg coordinate systems LC of a joint element J_hip (J9), J_knee (J11), J_ankle (J13), and J_MP (J14a), respectively, of each leg portion S2 are calculated in order according to expressions (4a) to (4d) given below. At this time, the positions of J_hip, J_knee, J_ankle, and J_MP in the Y-axis direction of the leg coordinate system LC (the normal line direction of the leg plane PL), that is, the Y coordinate components of J_hip, J_knee, J_ankle, and J_MP on the leg coordinate system LC, are all set to zero. This means that all J_hip, J_knee, J_ankle, and J_MP are capable of motions only on the leg plane PL.

$$U(J\_hip/LC) = (0,0,0)^T \quad (4a)$$

$$U(J\_knee/LC) = U(J\_hip/LC) + (-L10 \times \sin(\theta\_thigh), 0, -L10 \times \cos(\theta\_thigh))^T \quad (4b)$$

$$U(J\_ankle/LC) = U(J\_knee/LC) + (-L12 \times \sin(\theta\_crus), 0, -L12 \times \cos(\theta\_thigh))^T \quad (4c)$$

$$U(J\_MP/LC) = U(J\_ankle/LC) + (-L14 \times \sin(\theta\_foot), 0, -L14 \times \cos(\theta\_foot))^T \quad (4d)$$

Here, L10, L12, and L14 in expressions (4b), (4c), and (4d) denote the lengths of the thigh element S10, the crus element S12, and the foot element S14, respectively, and they are stored and retained in the memory of the arithmetic processing unit 18, as described above. Further, the vectors of the second terms of the right sides expressions (4b) to (4d) mean the position vector of the knee joint element J11 observed from the hip joint element J9, the position vector of the ankle joint element J13 observed from the knee joint element J11, and the position vector of the MP joint element J14a observed from the ankle joint element J13. The set of an X coordinate component and a Z coordinate component of each of the position vectors U(J_hip/LC), U(J_knee/LC), U(J_ankle/LC), and U(J_MP/LC) determined according to expressions (4a) to (4d) indicates a two-dimensional position on the leg plane PL.

The position vectors of the centers of gravity of the rigid elements of the leg portions S2 on the leg coordinate system LC are calculated by using the position vectors of the joint elements calculated as described above according to expressions (4b) to (4d). Specifically, the position vectors U(G_thigh/LC), U(G_crus/LC), and U(G_foot/LC) of the centers of gravity G_thigh (G10), G_crus (G12), and G_foot (G14) of the thigh element S10, the curs element S12, and the foot element S14, respectively, of each leg portion S2 are calculated according to expressions (5a) to (5c) shown below.

$$U(G\_thigh/LC)=(U(J\_knee/LC)+R(C\_thigh{\rightarrow}LC){\times}U(G\_thigh/C\_thigh) \tag{5a}$$

$$U(G\_crus/LC)=(U(J\_ankle/LC)+R(C\_crus{\rightarrow}LC){\times}U(G\_crus/C\_crus) \tag{5b}$$

$$U(G\_foot/LC)=(U(J\_MP/LC)+R(C\_foot{\rightarrow}LC){\times}U(G\_foot/C\_foot) \tag{5c}$$

Here, R(C_thigh→LC), R(C_crus→LC), and R(C_foot→LC) of expressions (5a) to (5c) are transformation tensors for accomplishing transformation from thigh coordinate system C_thigh (C10) to the leg coordinate system LC, from crus coordinate system C_crus (C12) to the leg coordinate system LC, and from foot coordinate system C_foot (C14) to the leg coordinate system LC, and they are determined by using θ_thigh, θ_crus, and θ_foot (refer to expressions (3a) to (3c)), which have been calculated previously. Further, U(G_thigh/C_thigh), U(G_crus/C_crus), and U(G_foot/C_foot) denote the position vectors of the centers of gravity of the rigid elements represented by the element coordinate systems of the rigid elements, and they are stored and retained in the memory of the arithmetic processing unit 18 beforehand, as described above.

The sets of X coordinate components and Z coordinate components of the position vectors U(G_thigh/LC), U(G_crus/LC), and U(G_foot/LC) determined according to the above expressions (5a) to (5c) indicate two-dimensional positions on the leg plane PL. The arithmetic processing explained above is the arithmetic processing of the two-dimensional leg posture/element center-of-gravity position calculating means 29.

Subsequently, the arithmetic processing of the three-dimensional joint/element center-of-gravity position calculating means 30 uses the transformation tensor determined by the transformation tensor creating means 28 and the positions (the positions in the leg coordinate system LC) of the centers of gravity of the joint elements and the rigid elements of each leg portion S2 determined by the two-dimensional leg posture/element center-of-gravity position calculating means 29 so as to determine the position vectors of the centers of gravity of the joint elements and the rigid elements of the rigid link model S1 in the body coordinate system BC.

The position vectors of the joint elements are calculated as described below. The calculation of the position vectors of the joint elements J9, J11 and J13 of the left leg portion S2 will be taken as an example for the explanation. First, if the portion between the two joints J9 and J9 of the waist element S6 is denoted by S6a and the length thereof is denoted by L6a, then the position vector U (J_left hip/BC) of the left hip joint J6 in the body coordinate system BC is given by the following expression (6a).

$$U(J\_left\ hip/BC)=(0,L6a/2,0)^T \tag{6a}$$

Further, the position vectors U(J_left knee/BC), U(J_left ankle/BC) and U(J_left MP/BC) of the left knee joint J11, the left ankle joint J13 and the left MP joint J14a, respectively, in the body coordinate system BC are determined in order according to expressions (6b) to (6d) shown below by using the transformation tensor R(LC→BC) and the position vectors U(J_left knee/LC), U(J_left ankle/LC) and U(J_left MP/LC) in the leg coordinate system LC (left LC) corresponding to the left leg portion S2.

$$U(J\_left\ knee/BC)=U(J\_left\ hip/BC)+R(LC{\rightarrow}BC){\times}U(J\_left\ knee/LC) \tag{6b}$$

$$U(J\_left\ ankle/BC)=U(J\_left\ knee/BC)+R(LC{\rightarrow}BC){\times}U(J\_left\ ankle/LC) \tag{6c}$$

$$U(J\_left\ MP/BC)=U(J\_left\ ankle/BC)+R(LC{\rightarrow}BC){\times}U(J\_left\ MP/LC) \tag{6d}$$

The position vectors of the joint elements of the right leg portion S2 in the body coordinate system BC are determined in the same manner described above.

Position vectors U(JU1/BC) and U(JU2/BC) of the upper body lower joint JU1 and the upper body upper joint JU2 of the upper body SU in the body coordinate system BC are determined in order according to the following expressions (7a) and (7b).

$$U(JU1/BC)=(0,0,L6b)^T \tag{7a}$$

$$U(JU2/BC)=U(JU1/BC)+R(C\_abdomen{\rightarrow}BC){\cdot}(0,0,L7)^T \tag{7b}$$

L6b in expression (7a) denotes the length of the portion S6b of the waist element S6, and L7 in expression (7b) denotes the length of the abdomen element S7. These lengths are stored and retained in the memory of the arithmetic processing unit 18 beforehand.

The position vectors of the centers of gravity of the rigid elements in the body coordinate system BC are calculated as follows. The position vectors U(G_thigh/BC), U(G_crus/BC) and U(G_foot/BC) of the centers of gravity of the thigh element S10, the crus element S12 and the foot element S14, respectively, in the body coordinate system BC are determined according to the expressions in which U(J_left knee/LC), U(J_left ankle/LC) and U(J_left MP/LC) of the right side of the above expressions (6b) to (6d) have been replaced by the position vectors U(G_thigh/LC), U(G_crus/LC) and U(G_foot/LC), respectively, of the centers of gravity of the thigh element S10, the crus element S12, and the foot element S14 calculated by the two-dimensional leg posture/element center-of-gravity position calculating means 29. The position vectors of the G_thigh, G_crus and G_foot in the body coordinate system BC are calculated separately for each leg portion S2.

A position vector U(G_waist/BC) of the center-of-gravity G6 of the waist element S6 is determined according to the following expression (8) from a position vector U(G_waist/C_waist) of the center-of-gravity G_waist in a waist coordinate system C_waist (C6) stored and retained beforehand.

$$U(G\_waist/BC)=R(C\_waist{\rightarrow}BC){\times}U(G\_waist/C\_waist) \tag{8}$$

where R(C_waist→BC) denotes a transformation tensor for transforming the waist coordinate system C_waist to the body coordinate system BC. In the present embodiment, C_waist is equivalent to the body coordinate system BC, so that R(C_waist→BC) is expressed by three-dimensional unit matrix. Hence, U(G_waist/C_waist) directly provides U(G_waist/BC).

Furthermore, the position vectors U(G_abdomen/BC) and U(G_chest/BC) of the centers of gravity G7 and G8 of the abdomen element S7 and the chest element S8, respectively, in the body coordinate system BC are determined according to expressions (9) to (10) shown below by using the transformation tensors R(C_abdomen→BC) and R(C_chest→BC) determined by the transformation tensor creating means 28, a position vector U(G_abdomen/C_abdomen) of the center-of-gravity of the abdomen element S7 in the abdomen coordinate system C_abdomen (C7), and a position vector U(G_chest/

C_chest) of the center-of-gravity of the chest element S8 in the chest coordinate system C_chest (C8) stored and retained beforehand.

$$U(G\_abdomen/BC)=U(JU1/BC)+R \\ (C\_abdomen \to BC) \cdot U(G\_abdomen/C\_abdomen) \quad (9)$$

$$U(G\_chest/BC)=U(JU2/BC)+R(C\_chest \to BC) \cdot U \\ (G\_chest/C\_chest) \quad (10)$$

U(JU1/BC) and U(JU2/BC) are determined according to expressions (7a) and (7b) shown above.

The arithmetic processing explained above is the arithmetic processing of the three-dimensional joint/element center-of-gravity position calculating means 30. The position vectors of the joint elements and the centers of gravity of the rigid elements calculated by the three-dimensional joint/element center-of-gravity position calculating means 30 mean the position vectors of the actual parts of the human being 1 corresponding thereto observed in the body coordinate system BC.

The arithmetic processing unit 18 carries out the arithmetic processing of the body coordinate system acceleration/angular velocity calculating means 31 and the body coordinate system inclination angle calculating means 32 while carrying out at the same time the arithmetic processing of the transformation tensor creating means 28, the two-dimensional leg posture/element center-of-gravity position calculating means 29 and the three-dimensional joint/element center-of-gravity position calculating means 30.

The arithmetic processing of the body coordinate system acceleration/angular velocity calculating means 31 determines the value (coordinate component value) of the acceleration vector of the origin of the body coordinate system BC in the body coordinate system BC as described below from the acceleration (translational acceleration) in the three-axis directions grasped from a detection output of the acceleration sensor 16 and the angular velocity about three axes grasped from a detection output of the gyro sensor 17. First, the acceleration and the angular velocity detected by the sensors 16 and 17, respectively, are vector amounts expressed by three-axis coordinate system (hereinafter referred to as the sensor coordinate system SC or the C_sensor) fixed to the sensors 16 and 17, so that they are converted into values in the body coordinate system BC. The conversion is accomplished by multiplying the acceleration vector and the angular velocity vector, which have been detected in the sensor coordinate systems SC, by a transformation tensor, which has been set in advance on the basis of the relative installation positional relationship (the relative posture relationship of the sensor coordinate systems SC in relation to a waist coordinate system C6 (=body coordinate system BC)) of the acceleration sensor 16 and the gyro sensor (angular velocity sensor) 17 relative to the waist 6. More specifically, if the detection value of the acceleration vector in the sensor coordinate system SC is denoted by ACC(sensor/SC), the acceleration vector obtained by converting the ACC(sensor/SC) into the body coordinate system BC is denoted by ACC(sensor/BC), the detection value of the angular velocity vector in the sensor coordinate system SC is denoted by ω(sensor/SC), and the angular velocity vector obtained by converting the ω(sensor/SC) into the body coordinate system BC is denoted by ω(sensor/BC), then the acceleration vector ACC(sensor/BC) and the angular velocity vector ω(sensor/BC) are determined according to expressions (11) and (12) given below. To be more specific, ACC(sensor/BC) and ω(sensor/BC) denote the acceleration vector and the angular velocity vector of the locations of the acceleration sensor 16 and the gyro sensor 17, respectively, and in this sense, the term "sensor" is added to the notations of ACC and ω. In this example, the locations of the acceleration sensor 16 and the gyro sensor 17 are substantially the same locations, and the same sensor coordinate system SC is used as the coordinate system for both sensors 16 and 17.

$$ACC(sensor/BC)=R(SC \to BC) \cdot ACC(sensor/SC) \quad (11)$$

$$\omega(sensor/BC)=R(SC \to BC) \cdot \omega(sensor/SC) \quad (12)$$

Figure 8:
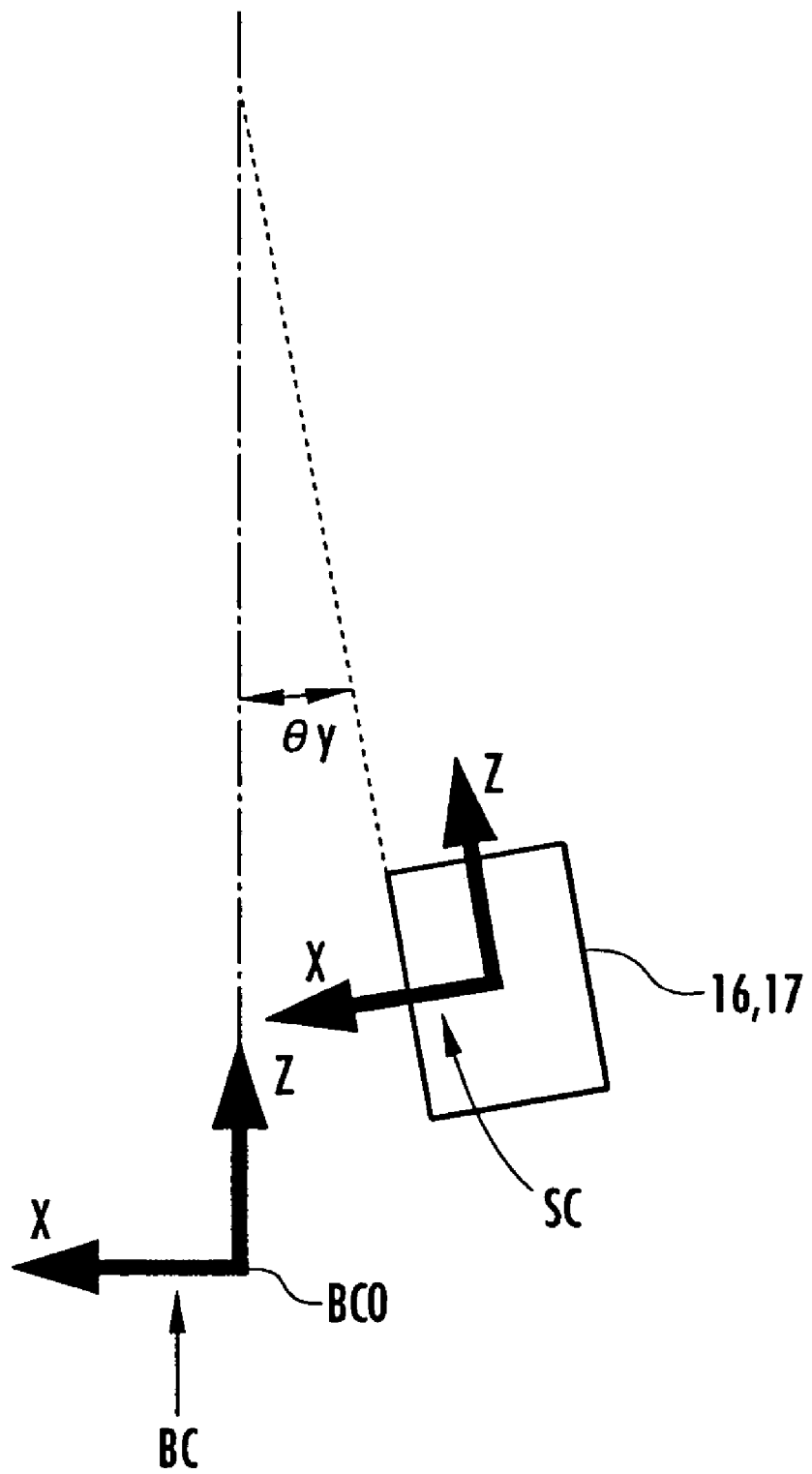
FIG. 8 is a diagram for explaining an example of coordinate conversion between a sensor coordinate system and a body coordinate system in the embodiment.

The transformation tensor R(SC→BC) is determined from a relative posture relationship between the sensor coordinate system SC and the body coordinate system BC (specifically, the inclination angle of each axis of the sensor coordinate system SC relative to each axis of the body coordinate system BC). For example, if the three axes (X, Y and Z axes) of the sensor coordinate system SC are inclined by an angle θy about the Y axis of the body coordinate system BC (the axis perpendicular to the paper surface of FIG. 8), as shown in FIG. 8, then the transformation tensor R(SC→BC) is represented by the matrix of the same form as that of the right side of the above expression (2). In this case, the acceleration sensor 16 and the gyro sensor 17 are fixed to the waist 6 with the body coordinate system BC provided thereon, so that the inclination angles of the axes of the sensor coordinate system SC relative to the axes of the body coordinate system BC are already known because they were actually measured when the acceleration sensor 16 and the gyro sensor 17 were mounted on the waist 6. Based on the inclination angles, the transformation tensor R(SC→BC) has been determined and stored and retained in the memory of the arithmetic processing unit 18. Supplementally, the acceleration sensor 16 or the gyro sensor 17 may be attached to a part other than the waist 6 (a corresponding rigid body associated with any one of the rigid elements of the rigid link model S1). In this case, the acceleration vector ACC(sensor/BC) and the angular velocity vector ω(sensor/BC) may be obtained by converting detection values in the sensor coordinate system SC into values in an element coordinate system of a rigid element to which the acceleration sensor 16 or the gyro sensor 17 is attached, and then by further converting the results into values in the body coordinate system BC by a transformation tensor. The transformation tensor in this case is determined on the basis of a detection value of the displacement amount (rotational angle) of a joint element between the rigid element to which the acceleration sensor 16 or the gyro sensor 17 is attached and the waist element S6.

In the arithmetic processing of the body coordinate system acceleration/angular velocity calculating means 31, after the acceleration vector ACC(sensor/BC) and the angular velocity vector ω(sensor/BC) are determined as described above, the acceleration vector of the origin of the body coordinate system BC, ACC(BCO/BC), is determined according to the following expression (13). "BCO" is a reference character denoting the origin of the body coordinate system BC.

$$ACC(BCO/BC) = \\ ACC(sensor/BC) + U(sensor/BC) \times \omega(sensor/BC)' + \\ \begin{bmatrix} 0 & U(sensor/BC)x & U(sensor/BC)x \\ U(sensor/BC)y & 0 & U(sensor/BC)y \\ U(sensor/BC)z & U(sensor/BC)z & 0 \end{bmatrix} \times \quad (13)$$

-continued $$\begin{bmatrix} \omega(sensor/BC)x^2 \\ \omega(sensor/BC)y^2 \\ \omega(sensor/BC)z^2 \end{bmatrix}$$

Note) ACC(BCO/BC) denotes a vector that becomes equal to a sensor output value when a sensor is installed at the origin of the body coordinate system BC, and the direction of the axis of the sensor is matched with the body coordinate system BC.

U(sensor/BC) in this expression (13) denotes a position vector of the acceleration sensor 16 and the gyro sensor 17. U(sensor/BC)x, U(sensor/BC)y and U(sensor/BC)z respectively denote coordinate component values of U(sensor/BC) in the body coordinate system BC according to the definition of a notation technique of coordinate component values of vectors in the present description discussed above. U(sensor/BC) is actually measured when the acceleration sensor 16 and the gyro sensor 17 are attached to the waist 6, and it is stored and retained in the memory of the arithmetic processing unit 18. ω(sensor/BC)x, ω(sensor/BC)y and ω(sensor/BC)z respectively denote coordinate component values of the angular velocity vector ω(sensor/BC) determined previously. Further, ω(sensor/BC)' denotes a first-order differential value of ω(sensor/BC), and a value thereof is calculated from time-series data of ω(sensor/BC) determined by the aforesaid expression (12) for each arithmetic processing cycle of the arithmetic processing unit 18.

The angular velocity at any portion in the waist element S6 is the same, and the angular velocity ω(BCO/BC) of the origin BCO of the body coordinate system BC fixed to the waist element S6 is equal to ω(sensor/BC). Accordingly, ω(sensor/BC) directly provides the angular velocity ω(BCO/BC) of the origin BCO of the body coordinate system BC. In other words, ω(BCO/BC)=ω(sensor/BC).

The acceleration sensor 16 also detects acceleration involved in gravity, so that the acceleration vector ACC(BCO/BC) determined as described above includes an inertial acceleration component attributable to gravity. In the present embodiment, the acceleration vector ACC(BCO/BC) of the origin BCO of the body coordinate system BC has been determined, considering the angular velocity of the waist element S6. Alternatively, however, the ACC(sensor/BC) determined in the above expression (11) may be directly used as the acceleration vector ACC(BCO/BC) of the origin BCO of the body coordinate system BC, because the angular velocities and their changing rates of the waist element S6 are relatively small.

Further, in the arithmetic processing of the body coordinate system inclination angle calculating means 32, the inclination angle (inclination angle of the Z axis of the body coordinate system BC) of the waist element S6 relative to the vertical direction (the direction of gravity) is calculated by a so-called Kalman filter from detection outputs of the acceleration sensor 16 and the gyro sensor 17. The calculating technique is publicly known, so that the explanation thereof will be omitted. The inclination angles calculated here are the inclination angles about two axes, namely, the horizontal axis in the longitudinal direction and the horizontal axis in the lateral direction.

The arithmetic processing unit 18 then executes the arithmetic processing of the overall center-of-gravity position calculating means 33. In the arithmetic processing of the overall center-of-gravity position calculating means 33, the position vector U(G_total/BC) of the overall center-of-gravity of the rigid link model S1 (the overall center-of-gravity of the human being 1; hereinafter referred to as G_total in some cases) in the body coordinate system BC is determined according to the following expression (14) from the position of center-of-gravity (the position vector in the body coordinate system BC) of each rigid element determined by the three-dimensional joint/element center-of-gravity position calculating means 30 and the weight of each rigid element preset as described above.

$$U(G\_total/BC) = \qquad (14)$$
$$\{U(G\_chest/BC) \times m\_chest + U(G\_abdomen/BC) \times m\_abdomen +$$
$$U(G\_waist/BC) \times m\_waist + U(G\_right\ thigh/BC) \times$$
$$m\_right\ thigh + U(G\_left\ thigh/BC) \times m\_left\ thigh +$$
$$U(G\_right\ crus/BC) \times m\_right\ crus +$$
$$U(G\_left\ crus/BC) \times m\_left\ crus +$$
$$U(G\_right\ foot/BC) \times m\_right\ foot +$$
$$U(G\_left\ foot/BC) \times m\_left\ foot\}/Total\ weight$$

"m_OO", such as m_chest, denotes the weight of the rigid element corresponding to the designation denoted by OO. As shown by this expression (14), the position vector of the overall center-of-gravity U(G_overall/BC) is determined by dividing the total sum of the products of the position vectors of the centers of gravity of the rigid elements of the rigid link model S1 in the body coordinate system BC and the weights of the rigid elements by the total weight of the human being 1 (=Total sum of the weights of all rigid elements).

Next, the arithmetic processing unit 18 carries out the calculation processing of the floor reaction force estimating means 34 and the floor reaction force acting point estimating means 35. In the arithmetic processing of the floor reaction force estimating means 34, it is first determined whether the motion of the human being 1 is in the two-leg supporting state, in which both legs 2 and 2 are in contact with the ground, or the one-leg supporting state, in which only one leg 2 is in contact with the ground, on the basis of detection outputs of the ground sensors 24 and 25. More specifically, it is determined that the motion is in the two-leg supporting state if one of the ground contact sensors 24 and 25 of one leg 2 outputs an ON signal indicating the contact with the ground, while one of the ground contact sensors 24 and 25 of the other leg 2 outputs the ON signal indicating the contact with the ground. It is determined that the motion is in the one-leg supporting state if one of the ground contact sensors 24 and 25 of one leg 2 out of two legs 2 and 2 outputs the ON signal indicating the contact with the ground, while neither of the ground contact sensors 24 and 25 of the other leg 2 outputs the ON signal indicating the contact with the ground. In the processing of the floor reaction force estimating means 34, a floor reaction force vector acting on each leg 2 is estimated by different arithmetic processing, depending on whether the motion is in the two-leg supporting state or the one-leg supporting state.

Figure 9:
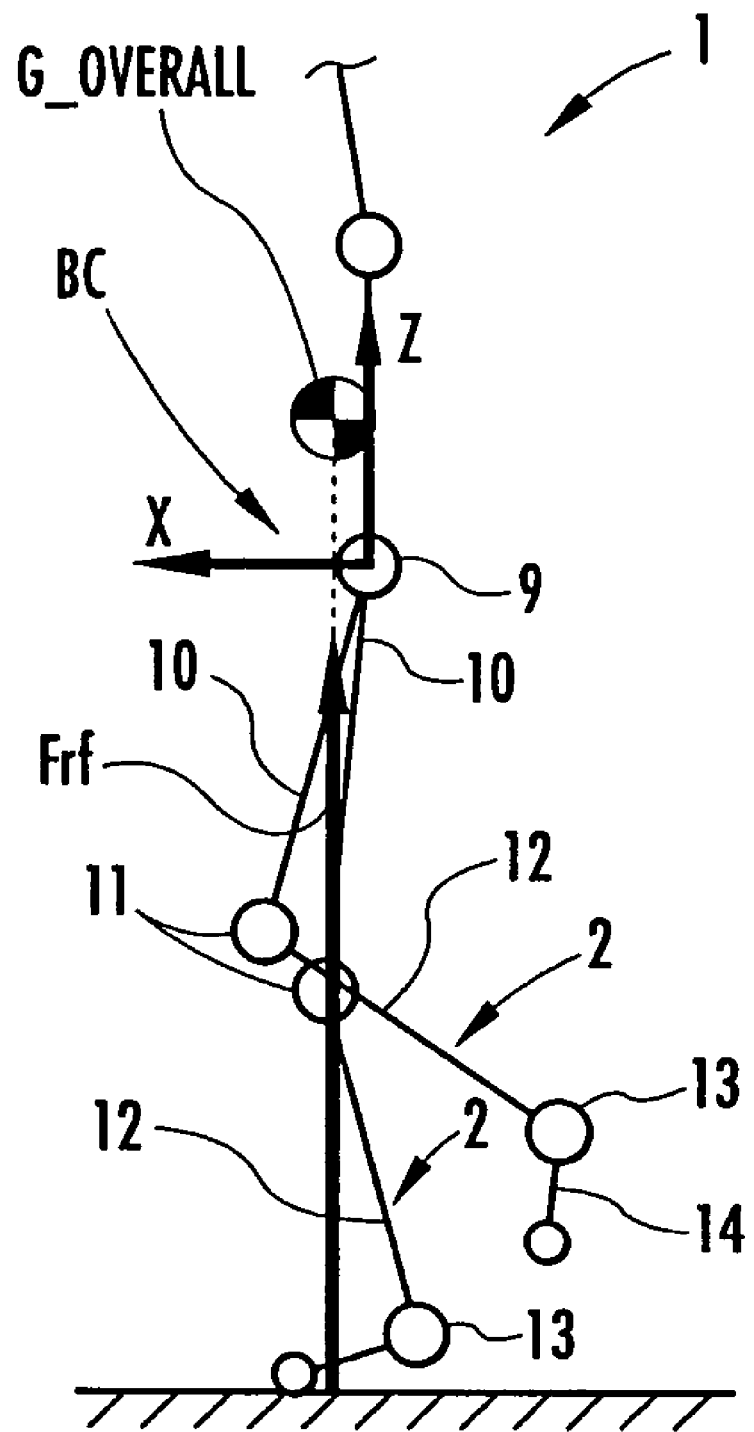
FIG. 9 is a diagram for explaining a technique for estimating a floor reaction force vector in a one-leg supporting state of the bipedal walking body, FIGS. 10(a) and (b) are diagrams for explaining a technique for estimating floor reaction force vectors in a two-leg supporting state of the bipedal walking body.
Figure 10:
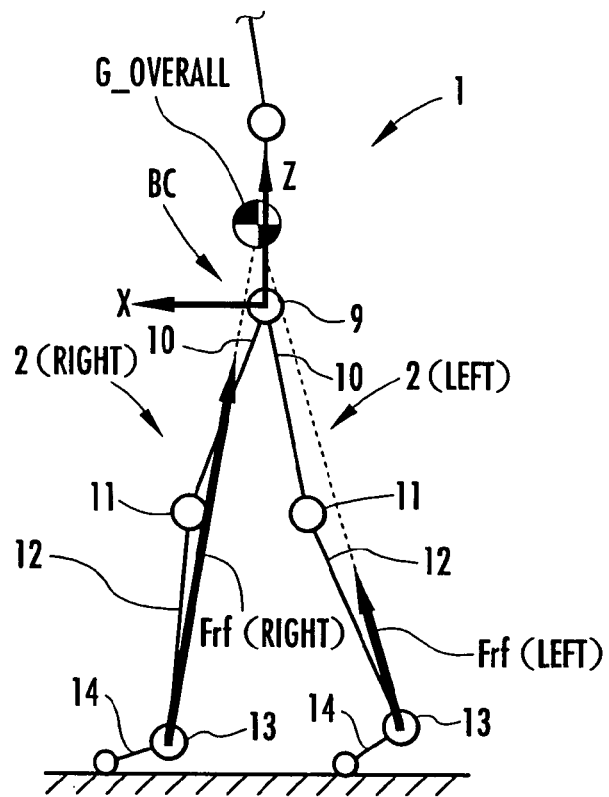
Figure 10:
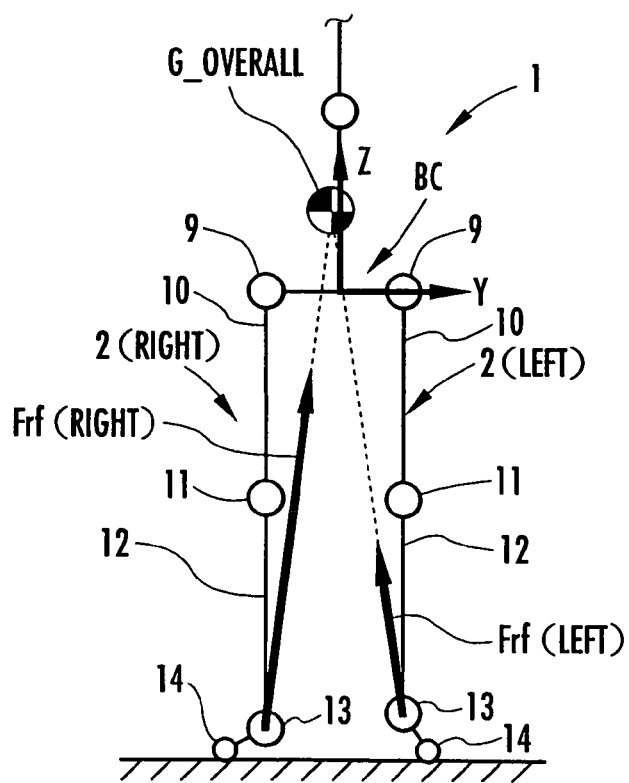

The basic concept of the processing for estimating a floor reaction force vector is the same as that in, for example, Japanese Unexamined Patent Application Publication No. 2003-89083 proposed previously by the present applicant. In the present embodiment, primarily the coordinate system used for the estimation processing is different from the technique described in the aforesaid publication or the like. This will be explained with reference to FIG. 9 and FIGS. 10(a) and (b). FIG. 9 illustrates the one-leg supporting state of the human being 1 observed on a sagittal plane, and FIGS. 10(a) and (b) illustrate the two-leg supporting state of the human being 1 observed on a sagittal plane and a front plane, respectively. The human being 1 in FIG. 9 and FIG. 10 is schematically shown in the form of a rigid link model. As shown in FIG. 9, if the motion state of the human being 1 is the one-leg supporting state, then a floor reaction force vector Frf (right leg/BC) acting on the leg 2 in contact with the ground (e.g., the right leg 2 in this case), that is, the floor reaction force vector acting on the right leg 2 in contact with the ground, which is expressed in terms of a coordinate component value in the body coordinate system BC, is calculated by the following expression (16) representing a dynamic equation related to a translational motion of the overall center-of-gravity G_overall in the body coordinate system BC.

$$\text{Frf}(\text{right leg}/BC) = \text{Total weight} \times (ACC(BCO/BC) + U(G\_overall/BC)'') \quad (16)$$

where U(G_overall/BC)″ denotes a second-order differential value of a position vector of the overall center-of-gravity G_overall in the body coordinate system BC, and it is calculated from time-series data of the position vector U(G_overall/BC) of the overall center-of-gravity G_calculated by the overall center-of-gravity position calculating means 33 for each arithmetic processing cycle of the arithmetic processing unit 18. The U(G_overall/BC)″ means a relative acceleration of the overall center-of-gravity G_overall relative to the origin of the body coordinate system BC. And, the ACC(BCO/BC) denotes an acceleration vector of the origin BCO of the body coordinate system BC calculated by the body coordinate system acceleration/angular velocity calculating means 31, and the value obtained by adding U(G_overall/BC)″ to the acceleration vector ACC(BCO/BC) means the actual acceleration of the overall center-of-gravity G_overall. Thus, the floor reaction force vector Frf (right leg/BC) is calculated according to expression (16) from the time-series data of the position vector of the G_overall calculated by the overall center-of-gravity position calculating means 33, the acceleration vector ACC(BCO/BC) of the origin of the body coordinate system BC calculated by the body coordinate system acceleration/angular velocity calculating means 31, and the total weight of the human being 1 (total weight of the rigid link model S1). In the case where the left leg 2 is in contact with the ground, the floor reaction force vector Frf (left leg/BC) is calculated by arithmetic operation of the right side of expression (16) in the same manner in the one-leg supporting state. In this case, the ACC(BCO/BC) includes an inertial acceleration component attributable to gravity, as mentioned above, and the floor reaction force vector Frf is expressed by means of the body coordinate system BC, so that it is unnecessary to consider gravitational acceleration or its direction. The floor reaction force vector Frf acting on the leg 2 not in contact with the ground is zero. In FIG. 9, for the convenience of illustration, the Z axis of the body coordinate system BC is shown in the vertical direction; however, expression (16) does not depend on the inclination of the body coordinate system BC.

Meanwhile, in the two-leg supporting state shown in FIGS. 10(a) and (b), the floor reaction force vector Frf (right leg/BC) acting on the right leg 2 and the floor reaction force vector Frf (left leg/BC) acting on the left leg 2 are calculated according to the following five relational expressions (17) to (21).

$$\text{Frf}(\text{right leg}/BC) + \text{Frf}(\text{left leg}/BC) = \text{Total weight} \times (ACC(BCO/BC) + U(G\_overall/BC)'') \quad (17)$$

$$\text{Frf}(\text{right leg}/BC)x : \text{Frf}(\text{right leg}/BC)z = U(G\_overall/BC)x - U(J\_right\ ankle/BC)x : U(G\_overall/BC)z - U(J\_right\ ankle/BC)z \quad (18)$$

$$\text{Frf}(\text{left leg}/BC)x : \text{Frf}(\text{left leg}/BC)z = U(G\_overall/BC)x - U(J\_left\ ankle/BC)x : U(G\_overall/BC)z - U(J\_left\ ankle/BC)z \quad (19)$$

$$\text{Frf}(\text{right leg}/BC)y : \text{Frf}(\text{right leg}/BC)z = U(G\_overall/BC)y - U(J\_right\ ankle/BC)y : U(G\_overall/BC)z - U(J\_right\ ankle/BC)z \quad (20)$$

$$\text{Frf}(\text{left leg}/BC)y : \text{Frf}(\text{left leg}/BC)z = ACC(G\_overall/BC)y - U(J\_left\ ankle/BC)y : U(G\_overall/BC)z - U(J\_left\ ankle/BC)z \quad (21)$$

The meanings of these expressions (17) to (21) will be explained. Expression (17) denotes a dynamic equation related to a translational motion of the overall center-of-gravity G_overall in the body coordinate system BC, the right side thereof being the same as the right side of the aforesaid expression (16). Expressions (18) to (21) are geometric relational expressions obtained on the assumption that the floor reaction force vector Frf(right leg/BC) and the floor reaction force vector Frf(left leg/BC) are the vectors directed from the ankle joint 13 of the right leg 2 and the ankle joint 13 of the left leg 2 toward the overall center-of-gravity G_overall, that is, the floor reaction force vector Frf and the position vector of the G_overall observed from the left ankle joint 13 have the same direction. In this case, expressions (18) and (19) are relational expressions observed on a sagittal plane (the XZ plane of the body coordinate system BC), while expressions (20) and (21) are relational expressions observed on the frontal plane (YZ of the body coordinate system BC plane). In FIG. 10, for the sake of convenience, the Z axis of the body coordinate system BC is shown in the vertical direction; however, expressions (17) to (21) do not depend on the inclination of the body coordinate system BC. In the present embodiment, the ankle joint 13 of each leg 2 means a particular portion in the vicinity of the bottom end portion of the leg 2.

To determine the floor reaction force vectors Frf(right leg/BC) and Frf(left leg/BC) in the two-leg supporting state, a simultaneous equation formed of the aforesaid expressions (17) to (21) is solved, with the coordinate component values of their vectors set as unknown numbers, so as to calculate the Frf(right leg/BC) and Frf(left leg/BC). More specifically, Frf (right leg/BC) and Frf(left leg/BC) are calculated from the time-series data of the position vector of the G_overall calculated by the overall center-of-gravity position calculating means 33, the acceleration vector ACC(BCO/BC) of the origin of the body coordinate system BC calculated by the body coordinate system acceleration/angular velocity calculating means 31, the total weight of the human being 1 (the total weight of the rigid link model S1), and U(J_right ankle/BC) and U(J_left ankle/BC) determined by the three-dimensional joint/element center-of-gravity position calculating means 30. Thus, in the present embodiment, the floor reaction force vectors Frf(right leg/BC) and Frf(left leg/BC) in the two-leg supporting state are calculated on the basis of the aforesaid relational expressions (17) to (21) described in the body coordinate system BC.

The Z-axis components of Frf(right leg/BC) and Frf(left leg/BC) can be determined by using either expressions (18) and (19) related to the sagittal plane or expressions (20) and (21) related to the frontal plane.

In the arithmetic processing of the floor reaction force acting point estimating means 35, first, a transformation tensor R(BC→IC) from the body coordinate system BC to an absolute coordinate system IC is created on the basis of an inclination angle of the waist element S6 relative to the vertical direction, which has been calculated by the body coordinate system inclination angle calculating means 32. Here, the absolute coordinate system IC is an orthogonal coordinate system with its Z axis extending in the vertical direction and it is a coordinate system in which the directions of the coordinate axes are the same as those of the body coordinate system BC in the aforesaid reference posture state. The transformation tensor R(IC→BC) from the absolute coordinate system IC to the body coordinate system BC is a transposed $R(BC→IC)^T$ of the transformation tensor R(BC→IC).

Subsequently, using the aforesaid transformation tensor R(BC→IC), the position vector U(G_overall/BC) of the overall center-of-gravity G_overall previously determined by the overall center-of-gravity position calculating means 33 and the position vectors U(J_ankle/BC) and U(J_MP/BC) of the ankle joint J13 and the MP joint J14a, respectively, of each leg portion S2 previously determined by the three-dimensional joint/element center-of-gravity position calculating means 30 are respectively multiplied by the aforesaid transformation tensor R(BC→IC) so as to calculate the position vectors U(G_overall/IC), U(J_ankle/IC) and U(J_MP/IC) observed in the absolute coordinate systems IC of the overall center-of-gravity G_overall, each ankle joint J13 and the MP joint J14a. These position vectors U(G_overall/IC), U(J_ankle/IC) and U(J_MP/IC) are the position vectors in the absolute coordinate system IC having the same origin as that of the body coordinate system BC. At this time, regarding the leg 2 that has been determined to be not in contact with the ground on the basis of detection outputs of the ground contact sensors 24 and 25, it is not necessary to calculate the position vectors U(J_ankle/IC) and U(J_MP/IC).

Figure 11:
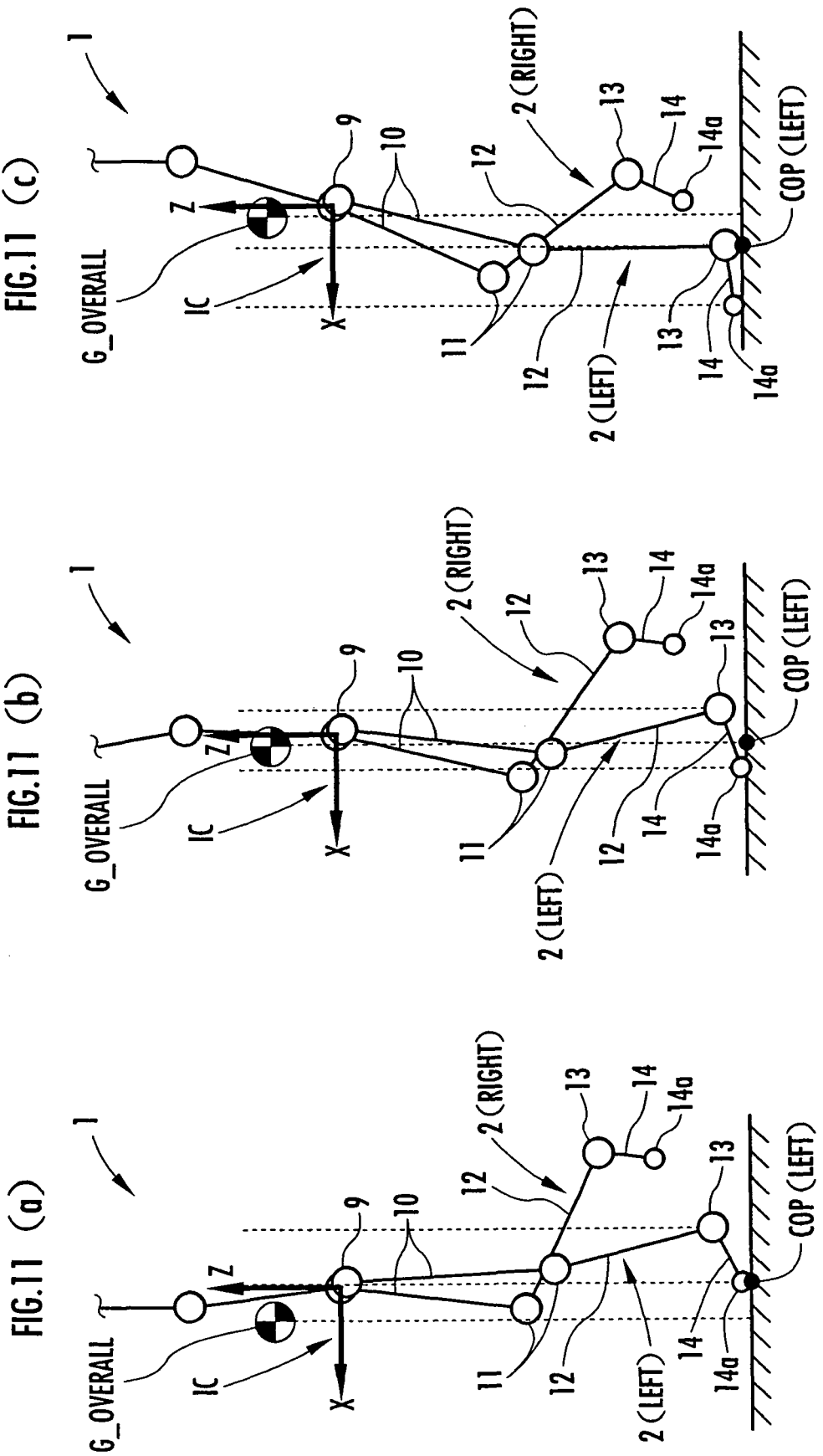
FIGS. 11(a) to (c) are diagrams for explaining a technique for estimating the acting points of floor reaction force vectors.
Figure 12:
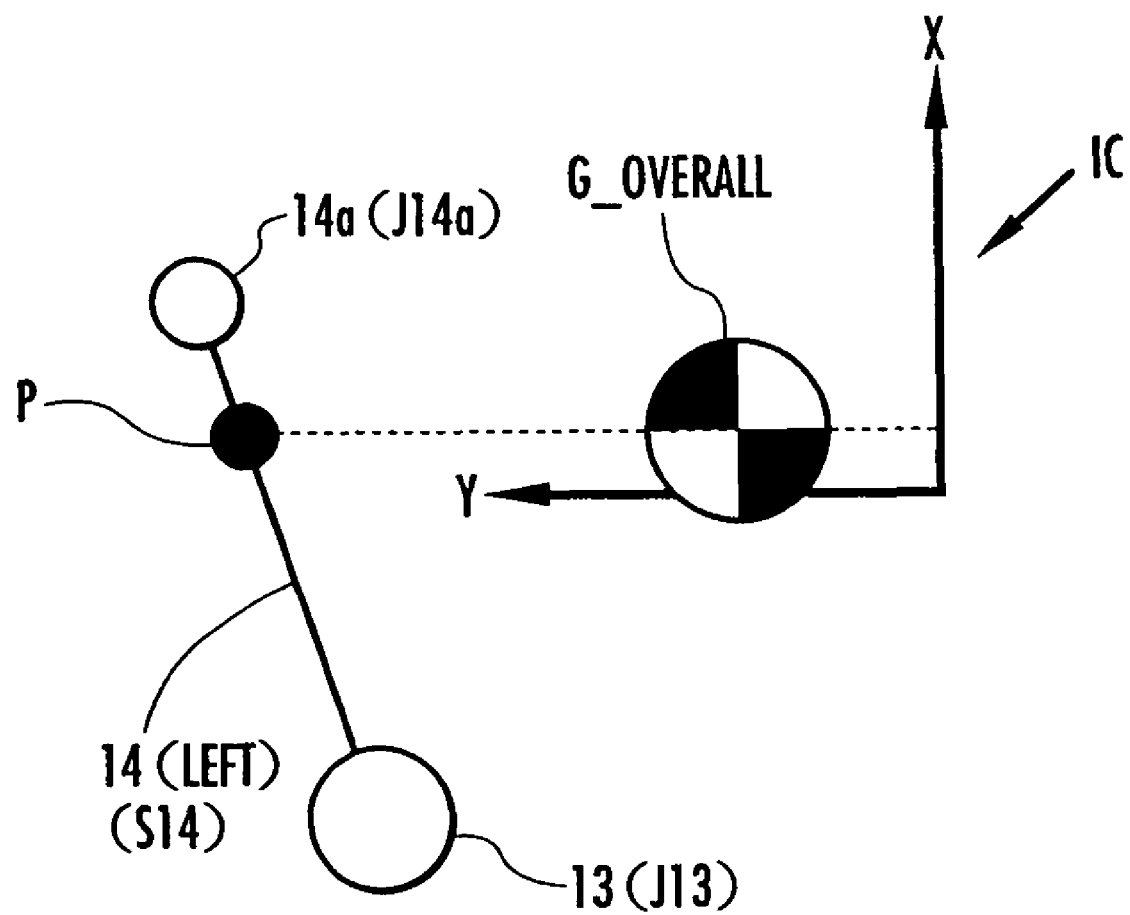
FIG. 12 is a diagram for explaining a technique for estimating a component in the Y-axis direction of the acting point of a floor reaction force vector in the state shown in FIG. 11(b)
Figure 13:
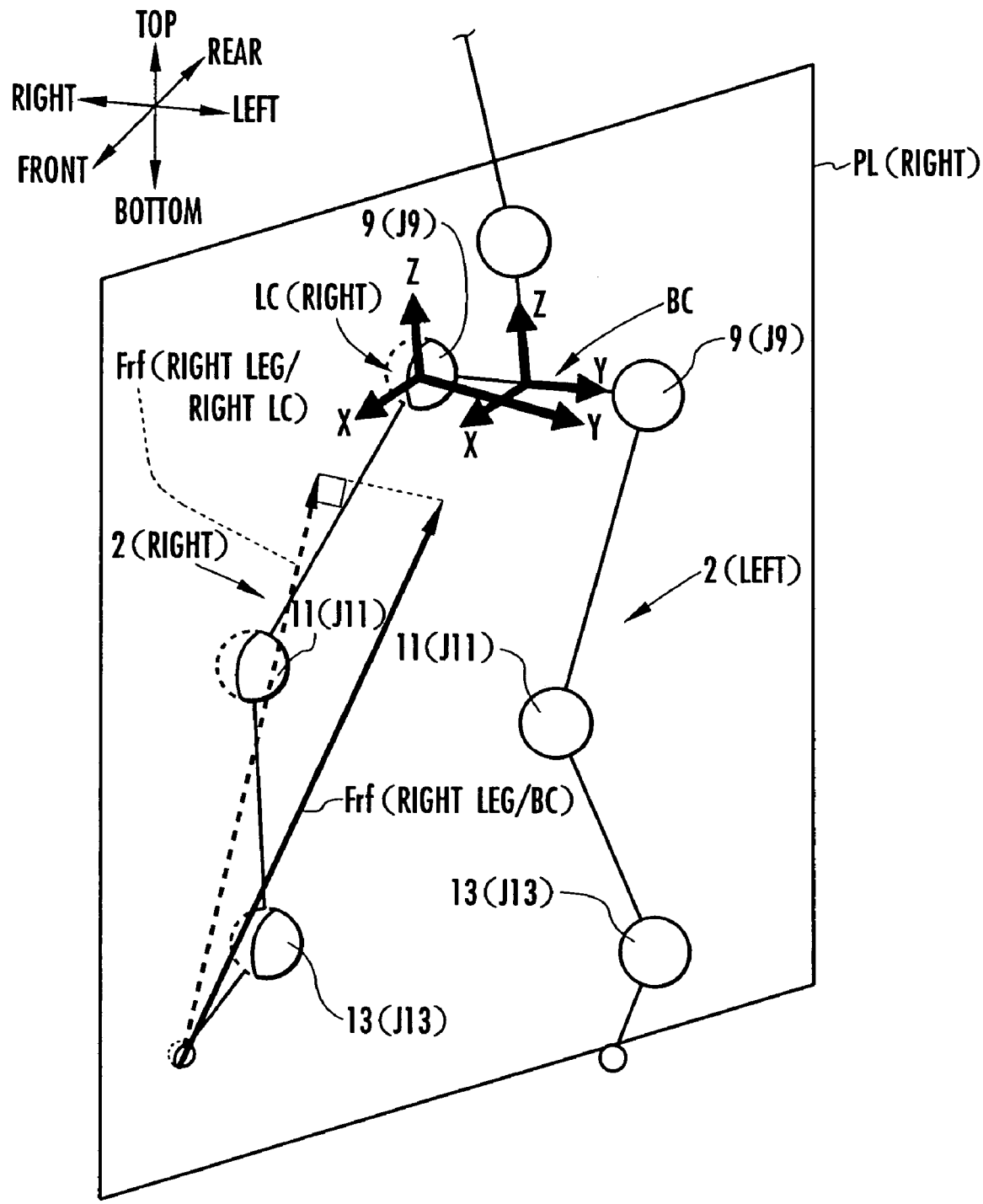
FIG. 13 is a diagram for explaining the processing of a leg plane projecting means shown in FIG. 6.

Subsequently, for each leg 2 that has been determined to be in contact with the ground on the basis of the detection outputs of the ground contact sensors 24 and 25, the position vector (the position vector in the absolute coordinate system IC) of a floor reaction force acting point, and an X-axis component and a Y-axis component of U(COP/IC) are determined on the basis of the size relationship among the X-axial components U(G_overall/IC)x, U(J_ankle/IC)x and U(J_MP/IC)x of the position vectors U(G_overall/IC), U(J_ankle/IC) and U(J_MP/IC), i.e., on the basis of the relative horizontal positional relationship in the longitudinal direction among the overall center-of-gravity G_overall, the ankle joint 13 and the MP joint 14a. This determining technique will be explained in further detail with reference to FIGS. 11(a) to 11(c) and FIG. 12. In the following explanation, it will be assumed that the left leg 2 is in contact with the ground. FIGS. 11(a) to (c) illustrate a state in which the left leg 2 of the human being 1 is in contact with the ground, as observed on a sagittal plane (the one-leg supporting state in these figures), and FIG. 12 is a plan view of the foot 14 in contact with the ground in the state shown in FIG. 11(b). FIG. 11 and FIG. 12 schematically show the human being 1 in the form of a rigid link model.

As shown in FIG. 11(a), if the overall center-of-gravity G_overall exists in front of the MP joint 14a of the left leg 2 in contact with the ground, that is, if U(G_overall/IC)x>U(J_left MP/IC)x, then the foot 14 of the left leg 2 is in contact with the ground, the contact being held mainly at its tiptoe portion. In this case, the floor reaction force acting point COP exists at a position substantially directly below the MP joint 14a of the foot 14. In this case, therefore, the X-axis and the Y-axis components of the position vector U(left COP/IC) of the floor reaction force acting point COP are equal to the X-axis and the Y-axis components, respectively, of the position vector U(J_left MP/IC) of the MP joint 14a. In other words, U(left COP/IC)x=U(J_left MP/IC)x and U(left COP/IC)y=U(J_left MP/IC)y.

Further, as shown in FIG. 11(c), if the overall center-of-gravity G_overall exists behind the ankle joint 13 of the left leg 2 in contact with the ground, that is, if U(G_overall/IC)x<U(J_left ankle/IC)x, then the foot 14 of the left leg 2 is in contact with the ground mainly at its heel portion. In this case, the floor reaction force acting point COP exists at a position substantially directly below the ankle joint 13 of the left leg 2. In this case, therefore, the X-axis and the Y-axis components of the position vector U(left COP/IC) of the floor reaction force acting point COP are equal to the X-axis and the Y-axis components, respectively, of the position vector U(J_left ankle/IC) of the ankle joint 13. In other words, U(left COP/IC)x=U(J_left ankle/IC)x and U(left COP/IC)y=U(J_left ankle/IC)y.

Further, as shown in FIG. 11(b), if the overall center-of-gravity G_overall exists between the ankle joint 13 and the MP joint 14a of the left leg 2 in the longitudinal direction, that is, if U(J_left MP/IC)x≦U(G_overall/IC)x≦U(J_left ankle/IC)x, then the floor reaction force acting point COP exists substantially directly below the overall center-of-gravity G_overall on the sagittal plane in the figure. In this case, therefore, the X-axis component of the position vector U(left COP/IC) of the floor reaction force acting point COP is equal to the X-axis component of the overall center-of-gravity G_overall. In other words, U(right,left COP/IC)x=U(G_overall/IC)x. The floor reaction force acting point COP exists on the contact surface between the foot 14 of the left leg 2 in contact with the ground and a floor surface (in this case, substantially the entire sole of the foot 14), and its position is considered to be on a segment obtained by projecting a segment that connects approximately the central point of the ankle joint 13 and the central point of the MP joint 14a onto the floor surface. Hence, the Y-axis component of the position vector U (right COP/IC) of the floor reaction force acting point COP is equal to the Y-axis component of a point P at which the values of the overall center-of-gravity G_overall and the X-axis component (the X-axis component in the absolute coordinate system IC) are the same on the axis of the foot element S14 related to the left leg 2 (on the segment connecting the central point of the ankle joint 13 and the central point of the MP joint 14a), as shown in FIG. 12. The value of the Y-axis component of the position vector U(right COP/IC) is determined according to the following expression (22), which is a proportionality relational expression.

$$U(\text{left } COP/IC)x - U(J\_\text{left ankle}/IC)x : U(J\_\text{left} \\ MP/IC)x - U(J\_\text{left ankle}/IC)x = U(\text{left } COP/IC)y - \\ U(J\_\text{left ankle}/IC)y : U(J\_\text{left } MP/IC)y - U(J\_\text{left} \\ \text{ankle}/IC)y \quad (22)$$

Further, the Z-axis component of the position vector U(left COP/IC) of the floor reaction force acting point is equal to the Z-axis component of a point that is away from the ankle joint 13 (ankle element J13) of the left leg 2 downward in the vertical direction by a predetermined value H0 (>0) set beforehand. In other words, U(left COP/IC)z=U(J_left ankle/IC)z−H0. Here, the predetermined value H0 denotes the vertical distance from the floor surface to the center of the ankle joint 13 in the aforesaid reference posture state (more precisely, a state in which substantially the entire sole of the foot 14 is in contact with the horizontal floor surface), and it is actually measured and stored and retained in the memory of the arithmetic processing unit 18 in advance. The predetermined value H0 may be actually measured on each of the right and left legs 2 separately, or an actually measured value on one of the legs 2 may be used for both right and left legs 2.

In the present embodiment, as described above, the position vector U(left COP/IC) of the floor reaction force acting point of the floor reaction force vector Frf acting on the left leg when the left leg 2 is in contact with the ground is determined. The same applies when the right leg 2 is in contact with the ground. In this case, in the two-leg supporting state, the position vector of the floor reaction force acting point on each of the legs 2 is determined, as described above.

In the present embodiment, the aforesaid predetermined value H0 used to determine the Z-axis component of the position vector U(COP/IC) of the floor reaction force acting point has been set to a constant value. Alternatively, however, if the ground contact sensors 24 and 25 indicate that only the tiptoe side of the foot 14 is in contact with the ground, that is, if only the ground contact sensor 25 outputs the ON signal, which indicates the contact with the ground, then the difference in the Z-axis component between the position vectors U(J_ankle/IC) and U(J_MP/IC) of the ankle joint 13 and the MP joint 14a, respectively, of the leg 2 in contact with the ground (U(J_ankle/IC)z-U(J_MP/IC)z), i.e., the vertical distance between the ankle joint 13 and the MP joint 14a, may be used in place of the aforesaid predetermined-value H0. This permits higher accuracy of U(COP/IC) to be achieved.

In the arithmetic processing of the floor reaction force acting point estimating means 35, lastly, the position vector U(COP/IC) of the floor reaction force acting point determined on each leg 2 in contact with the ground, as described above, is multiplied by an inverted transformation tensor R(IC→BC), which is a transposed transformation tensor R(BC→IC) obtained previously, thereby determining the value U(COP/BC) in the body coordinate system BC of the position vector of the floor reaction force acting point.

Next, the arithmetic processing unit 18 executes the arithmetic processing of the aforesaid leg plane projecting means 36. In this processing, the acceleration vector ACC(BCO/BC) and the angular velocity vector ω(BCO/BC) of the origin BCO of the body coordinate system BC calculated by the body coordinate system acceleration/angular velocity calculating means 31, the floor reaction force vectors Frf(right leg/BC) and Frf(left leg/BC) calculated by the floor reaction force estimating means 34, and the position vector U(COP/BC) of the floor reaction force acting point COP calculated by the floor reaction force acting point estimating means 35 are projected onto the leg plane PL corresponding to each leg portion S2 by using a transformation tensor R(BC→LC) (=R (LC→BC) T) obtained by transposing the transformation tensor R(LC→BC), which has been created by the transformation tensor creating means 28.

Specifically, the acceleration vector ACC(BCO/BC) and the angular velocity vector ω(BCO/BC) are respectively multiplied by the transformation tensor R(BC→LC), as shown in expressions (23a) and (23b) shown below, so as to determine the acceleration vector ACC(BCO/LC) and the angular velocity vector ω(BCO/LC) observed from each leg coordinate system LC.

$$ACC(BCO/LC)=R(BC{\rightarrow}LC){\times}ACC(BCO/BC) \quad (23a)$$

$$\omega(BCO/LC)=R(BC{\rightarrow}LC){\times}\omega(BCO/BC) \quad (23b)$$

The acceleration vector ACC(BCO/LC) and the angular velocity vector ω(BCO/LC) are determined separately for the leg coordinate system LC related to the left leg portion S2 and the leg coordinate system LC related to the right leg portion S2, respectively.

Similarly, the floor reaction force vector Frf (right leg/BC) and Frf(left leg/BC) are respectively multiplied by the transformation tensors R(BC→right LC) and R(BC→left LC), as shown in expressions (23c) and (23d) shown below, so as to determine the floor reaction force vector Frf (right leg/right LC) and Frf(left leg/left LC) observed from each leg coordinate system LC.

$$Frf(right\ leg/right\ LC)=R(BC{\rightarrow}right\ LC){\times}Frf(right\ leg/BC) \quad (23c)$$

$$Frf(left\ leg/left\ LC)=R(BC{\rightarrow}left\ LC){\times}Frf(left\ leg/BC) \quad (23d)$$

Further, the position vector U(COP/BC) of the floor reaction force acting point COP related to each leg 2 in contact with the ground is multiplied by the transformation tensor R(BC→LC) corresponding to the leg 2 in contact with the ground, as shown in expression (23e) given below, so as to determine the position vector U(COP/LC) of the floor reaction force acting point COP observed from the leg coordinate system LC corresponding to the leg 2.

$$U(COP/LC)=R(BC{\rightarrow}LC){\times}U(COP/BC) \quad (23e)$$

If only one leg 2 is in contact with the ground, then the position vector U(COP/LC) is determined only on that leg 2. If both legs 2 are in contact with the ground, then the position vector U(COP/LC) is determined on each of the right and left legs 2.

Here, the set of an X coordinate component and a Z coordinate component of each of the acceleration vector ACC (BCO/LC), the floor reaction force vectors Frf (right leg/right LC) and Frf (left leg/left LC), and the position vector of the floor reaction force acting point U(COP/LC) is provided in the form of a vector of a two-dimensional amount obtained by projecting a vector (three-dimensional amount) in the body coordinate system BC corresponding to each of them onto each leg plane PL (XZ plane in the leg coordinate system LC). Referring to, for example, FIG. 13, if the floor reaction force vector Frf related to the right leg 2 in the body coordinate system BC (right leg/right LC) is a vector indicated by the solid line in the figure, then the set of the X coordinate component and the Z coordinate component of the floor reaction force vector Frf (right leg/right LC) will provide the vector on the leg plane PL (right), as indicated by the dashed line in the figure.

The rotational motion of the leg 2 on the leg plane PL is a rotational motion about the axis in the normal line direction of the leg plane PL (Y-axis direction of the leg coordinate system LC), so that the result obtained by projecting the angular velocity vector ω(BCO/BC) onto the leg plane PL provides a Y coordinate component of the angular velocity vector ω(BCO/LC) in the leg coordinate system LC determined according to expression (23b) shown above.

In the following explanation, the acceleration vector ACC (BCO/LC), the floor reaction force vectors Frf (right leg/right LC) and Frf (left leg/left LC), and the position vector of the floor reaction force acting point U(COP/LC) will mean two-dimensional vectors formed of sets of their X coordinate components and Z coordinate components. For instance, the acceleration vector ACC(BCO/LC) means (ACC(BCO/LC) x, ACC(BCO/LC)z)$^T$. The values of the angular velocity ω on the leg plane PL will be denoted by ω(BCO/LC)y.

Next, the arithmetic processing unit 18 carries out the arithmetic processing by the joint moment estimating means 37. The following will explain the outline of the arithmetic processing of the joint moment estimating means 37. The computation of an inverse dynamic model based on a dynamic equation related to the translational motion and the rotational motion of each of the foot element S14, the crus element S12 and the thigh element S10 of each leg portion S2 calculates the joint moment of the joint elements J—ankle, J_knee and J_hip of the foot element S14, the crus element S12 and the thigh element S10 at their end points adjacent to the waist element S6 in order. In this case, the inverse dynamic model is handled on the leg plane PL (the XZ plane of the leg coordinate system LC) for each leg portion S2. The basic concept of this calculation processing is the same as that proposed in Japanese Unexamined Patent Publication Application No. 2003-89083 by the present applicant except for the planes and coordinate systems that handle the inverse dynamic model.

Figure 14:
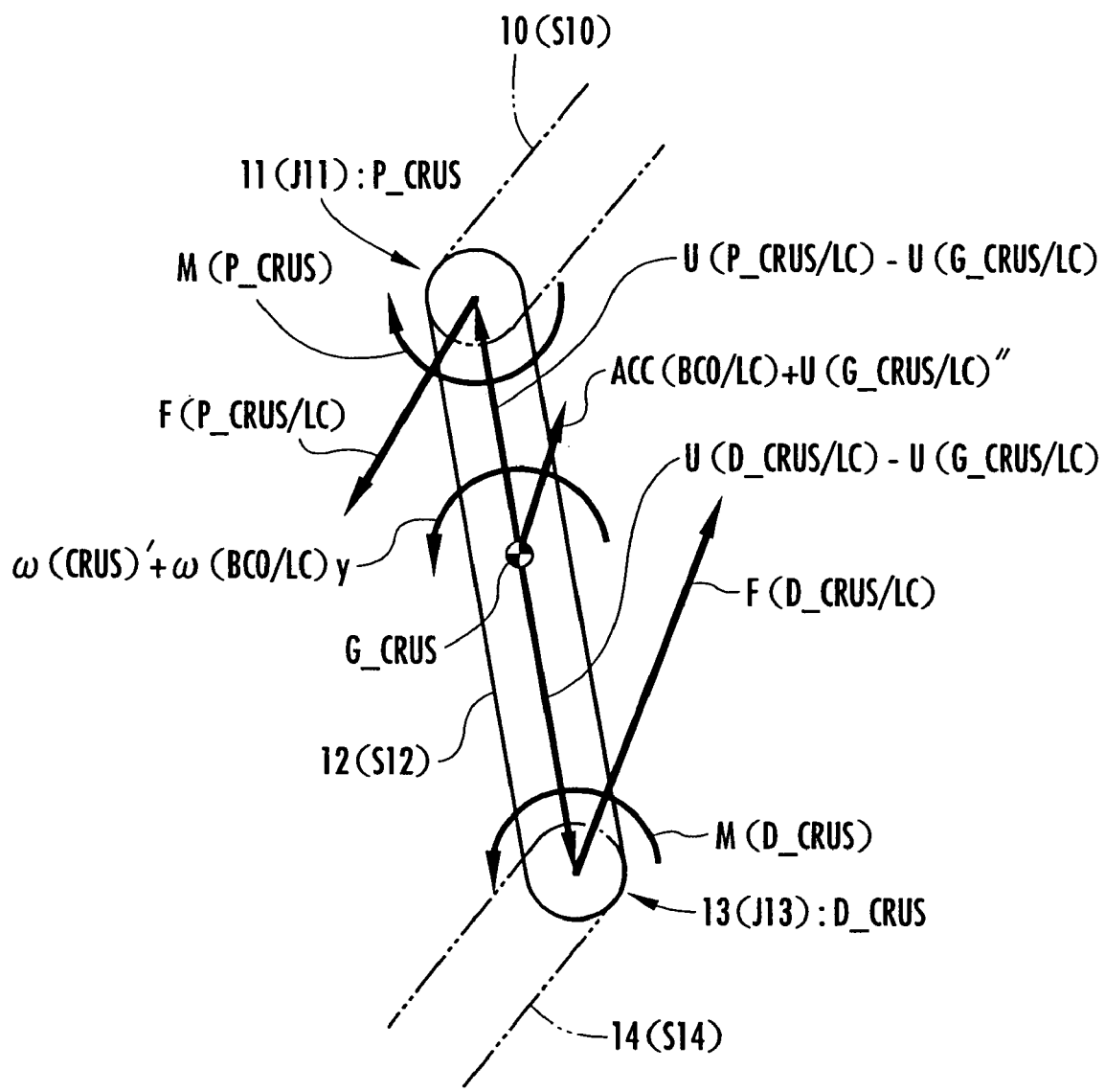
FIG. 14 is a diagram for explaining the arithmetic processing by an inverse dynamic model for determining joint moments.

To explain specifically, the dynamic equations of the translational motions of the foot element S14, the crus element S12 and the thigh element S10 of each leg portion S2 on the leg plane PL are given by expressions (24) to (26) shown below. In the following explanation, generally, there are cases where, of both ends of each rigid element of the foot element S14, the crus element S12 and the thigh element S10, one end closer to the waist element S6 is denoted by "P_OO", while the other end farther therefrom is denoted by "D_OO" (OO denotes the designation of a rigid element). For example, as shown in FIG. 14, the end of the crus element S12 adjacent to the knee joint J_knee (J11) is denoted as "P—crus," while the end thereof adjacent to the ankle joint J_ankle (J13) is denoted as "D—crus." The term "one end adjacent to" does not means that its distance to the waist element S6 is shorter; instead, it means that it has a fewer rigid elements present between the one end and the waist element S6. Similarly, "the other end farther from" means that it has more rigid elements between the other end and the waist element S6.

$$F(P\_foot/LC) = m\_foot \times (ACC(BCO/LC) + U(G\_foot/LC)") - Frf(leg/LC) \quad (24)$$

$$F(P\_crus/LC) = m\_crus \times (ACC(BCO/LC) + U(G\_crus/LC)") - F(D\_crus/LC) \quad (25)$$

$$F(P\_thigh/LC) = m\_thigh \times (ACC(BCO/LC) + U(G\_thigh/LC)") - F(D\_thigh/LC) \quad (26)$$

The two F(P_OO/BC) and F(D_OO/BC) appearing in the above expressions (24) to (26) mean reaction forces applied to the ends of rigid elements, which have the designations denoted by the OO, from an object that contacts them (two-dimensional translational force vectors on the leg plane PL). Therefore, based on the principle of action and counteraction, F(D_crus/BC)=−F(P_foot/BC), F(D_thigh/BC)=−F(P_crus/BC). In expression (24) related to the foot element S14, the end of the foot element S14 that is farther from the waist element S6 is regarded as the floor reaction force acting point COP, and the floor reaction force vector Frf (leg/LC) determined by the leg plane projecting means 36 is used as a reaction force acting on the end (the floor reaction force acting point COP) from the floor.

Further, U(G_foot/LC)", U(G_crus/LC)" and U(G_thigh/LC)" mean the second-order differential values of the position vectors of the centers of gravity G_foot, G_crus and G_thigh in the leg coordinate system LC previously calculated by the aforesaid two-dimensional leg posture/element center-of-gravity position calculating means 29 (more precisely, the sets of X coordinate components and Z coordinate components of the position vectors), that is, the relative accelerations (two-dimensional vectors) of the centers of gravity G_foot, G_crus and G_thigh relative to the origin of the leg coordinate system LC, which are observed on the leg plane PL. In this case, the acceleration vector of the origin of the leg coordinate system LC (the center of the hip joint J9) on the leg plane PL is substantially the same as the acceleration vector ACC(BCO/LC) of the origin of the body coordinate system BC. Hence, adding U(G_foot/LC)", U(G_crus/LC)" and U(G_thigh/LC)" to the acceleration vector ACC(BCO/LC) provides the actual acceleration vectors of the centers of gravity G_foot, G_crus and G_thigh on the leg plane PL.

FIG. 14 representatively illustrates a relationship of the parameters of expression (25) related to the crus element S12.

Accordingly, F(P_foot/LC), that is, the translational force acting on the ankle joint J_ankle (a two-dimensional vector on the leg plane PL), is determined by computing the right side of expression (24) from the floor reaction force vector Frf(leg/LC) and the acceleration vector ACC(BCO/LC) determined by the leg plane projecting means 36, the relative acceleration vector U(G_foot/LC)" obtained from the time-series data of the position vector U(G_foot/LC) of the center-of-gravity of the foot element S14 determined by the aforesaid two-dimensional leg posture/element center-of-gravity position calculating means 29, and a weight m_foot of the foot element S14. Furthermore, F(P_crus/LC), that is, the translational force acting on the knee joint J_knee (a two-dimensional vector on the leg plane PL), is determined by computing the right side of expression (25) from the determined F(P_foot/LC) (=−F(D_crus/LC)), the acceleration vector ACC(BCO/LC) determined by the leg plane projecting means 36, the relative acceleration vector U(G_crus/LC)" obtained from the time-series data of the position vector U(G_crus/LC) of the center-of-gravity of the crus element S12 determined by the two-dimensional leg posture/element center-of-gravity position calculating means 29, and a weight m_crus of the crus element S12. Similarly, by using the determined F(P_crus/LC) (=−F(D_thigh/LC)) or the like, the right side of expression (26) is computed to determine F(P_thigh/LC), that is, the translational force (the two-dimensional vector on the leg plane PL) acting on the hip joint J_hip. Thus, the reaction force vectors (translational force vectors) acting on the joint elements J_ankle, J_knee and J_hip are calculated in order according to the dynamic equations (24) to (26) shown above.

Next, the dynamic equations of the rotational motions of the foot element S14, the crus element S12 and the thigh element S10 (the rotational motions about the axes perpendicular to the leg plane PL that pass the individual centers of gravity) are given by expressions (27) to (29) shown below.

$$M(P\_foot) = I\_foot \times (\omega(foot)' + \omega(BCO/LC)y') - \\ (U(COP/LC) - U(G\_foot/LC)) \times Frf(leg/LC) - \\ (U(P\_foot/LC) - U(G\_foot/LC)) \times F(P\_foot/LC) \quad (27)$$

$$M(P\_crus) = I\_crus \times (\omega(crus)' + \omega(BCO/LC)y') - \\ (U(D\_crus/LC) - U(G\_crus/LC)) \times F(D\_crus/LC) - \\ (U(P\_crus/LC) - U(G\_crus/LC)) \times F(P\_crus/LC) - M(D\_crus) \quad (28)$$

$$M(P\_thigh) = I\_thigh \times (\omega(thigh)' + \omega(BCO/LC)y') - \\ (U(D\_thigh/LC) - U(G\_thigh/LC)) \times F(D\_thigh/LC) - \\ \{(U(P\_thigh/LC) - U(G\_thigh/LC)) \times F(P\_thigh/LC) - \\ M(D\_thigh) \quad (29)$$

Here, M(P_OO) and M(D_OO) appearing in the above expressions (26) to (28) mean reaction force moments applied to the ends of rigid elements, which have the designations denoted by the OO, from an object that contacts them (the moments about an axis perpendicular to the leg plane PL (about the axis parallel to the Y axis of the leg coordinate system LC)) (see FIG. 14). Therefore, based on the principle of action and counteraction, M(D_crus)=−M(P_foot), M(D_thigh)=−M(P_crus). Further, I_foot, I_crus and I_thigh are inertial moments about the centers of gravity of the foot element S14, the crus element S12 and the thigh element S10, respectively. They are determined on the basis of actual measurement data or the like and stored and retained in the memory of the arithmetic processing unit 18, as for the weights of the rigid elements. In addition, ω(foot)', ω(crus)' and ω(thigh)' mean the first-order differential values of relative angular velocities ω(foot), ω(crus) and ω(thigh) (relative angular velocities about the axis perpendicular to the leg plane PL) of the foot element S14, the crus element S12 and the thigh element S16, respectively, which are observed from the leg coordinate system LC, i.e., relative angular velocities. These are given as the second-order differential values of inclination angles θ_foot, θ_crus and θ_thigh of the foot element S14, the crus element S12 and the thigh element S10 determined by the aforesaid two-dimensional leg posture/element center-of-gravity position calculating means 29, as shown by the following expressions (29a) to (29c).

$$\omega(foot)' = \theta\_foot'' \qquad (29a)$$

$$\omega(crus)' = \theta\_crus'' \qquad (29b)$$

$$\omega(thigh)' = \theta\_thigh'' \qquad (29c)$$

And, ω(BCO/LC)y' denotes a first-order differential value of the actual angular velocity ω(BCO/LC)y of the origin BCO of the body coordinate system BC determined by the leg plane projecting means 36. The results obtained by adding ω(foot)', ω(crus)' and ω(thigh)' to the first-order differential value ω(BCO/LC)y' denote the actual angular velocities (the angular velocities about the axis perpendicular to the leg plane PL) of the foot element S14, the crus element S12 and the thigh element S14, respectively.

FIG. 14 representatively illustrates a relationship of the parameters of expression (28) related to the crus element S12.

The joint moment estimating means 37 lastly determines, according to the above expressions (27) to (29), joint moments M(P_foot), M(P_crus) and M(P_thigh) in sequence. Specifically, the joint moment M(P_foot), i.e., the moment about the axis perpendicular to the leg plane PL that acts on the ankle joint 13, is determined by computing the right side of the above expression (27) from the floor reaction force vectors Frf(leg/LC) and U(COP/LC) determined by the leg plane projecting means 36, the angular acceleration ω(BCO/LC)y' grasped from the time-series data of the angular velocity ω(BCO/LC)y determined by the leg plane projecting means 36, the relative angular acceleration ω(foot)' (=θfoot'') grasped from the time-series data of the inclination angle θ_foot determined by the aforesaid two-dimensional leg posture/element center-of-gravity position calculating means 29, the position vectors U(G_foot/LC) and U(P_foot/LC)(=U(J_ankle/LC)(more precisely, the sets of X coordinate components and Z coordinate components of the position vectors) determined by the two-dimensional leg posture/element center-of-gravity position calculating means 29, the reaction force F(P_foot/LC) previously determined according to the above expression (24), and a preset inertial moment I_foot.

Further, the joint moment M(P_crus), i.e., the moment about the axis perpendicular to the leg plane PL that acts on the knee joint 11, is determined by computing the right side of the above expression (28) from the determined joint moment M(P_foot)(=−M(D_crus)), the reaction forces F(P_foot/LC) (=−F(D_crus/LC)) and F(P_crus/LC) previously determined according to the above expressions (24) and (25), the angular acceleration ω(BCO/LC)y' grasped from the time-series data of the angular velocity ω(BCO/LC)y determined by the leg plane projecting means 36, the relative angular acceleration ω(crus)' (=θ_crus'') grasped from the time-series data of the inclination angle θ_crus determined by the aforesaid two-dimensional leg posture/element center-of-gravity position calculating means 29, the position vectors U(G_crus/LC) and U(P_crus/LC)(=U(J_knee/LC)) and U(D_crus/LC)(=U(J_ankle/LC)) (more precisely, the sets of X coordinate components and Z coordinate components of the position vectors) determined by the two-dimensional leg posture/element center-of-gravity position calculating means 29, and a preset inertial moment I_crus. Similarly, using the determined M(P_crus)(=−M(D_thigh)) or the like, the right side of the expression (29) is computed to determine M(P_thigh), that is, the moment about the axis perpendicular to the leg plane PL, which acts on the hip joint 9.

In the present embodiment, the inertial moments I_foot, I_crus and I_thigh of the rigid elements of each leg portion S2 have been considered; however, they generally take values sufficiently close to zero. For this reason, in the computation of expressions (27) to (29), the terms including the inertial moments I_foot, I_crus and I_thigh may be omitted. In this case, there is no need to grasp the angular velocities or angular accelerations of the foot element S14, the crus element S12 and the thigh element S10.

As described above, in the arithmetic processing of the joint moment estimating means 37, the joint moments M(P_foot), M(P_crus) and M(P_thigh) about the axis perpendicular to the leg plane PL of the ankle joint 13, the knee joint 11 and the hip joint 9, respectively, of each leg 2 are calculated in order, beginning with the ankle joint 13 side. The joint moments determined as described above are used for controlling a device for assisting, for example, a human being 1 with walking (a device incorporating an electric motor capable of imparting auxiliary torques to the ankle joint 13, the knee joint 11 and the hip joint 9). In this case, since the joint moments M(P_foot), M(P_crus) and M(P_thigh) are moments about the axis perpendicular to the leg plane PL, i.e., the moments in the directions in which the legs 2 bend or stretch, it is possible to properly impart the torque that aids particularly bending/stretching motions of each leg 2.

Figure 15:
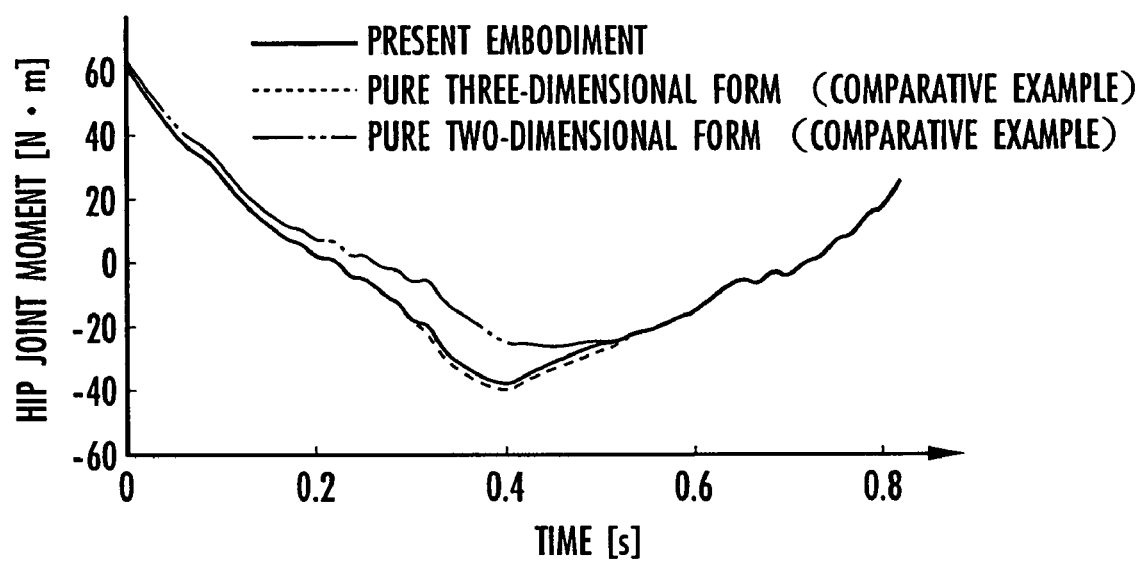
FIG. 15 and FIG. 16 are graphs showing the transition of an estimated value of the joint moment of a hip joint and an estimated value of the joint moment of a knee joint, respectively, when the human being walks.
Figure 16:
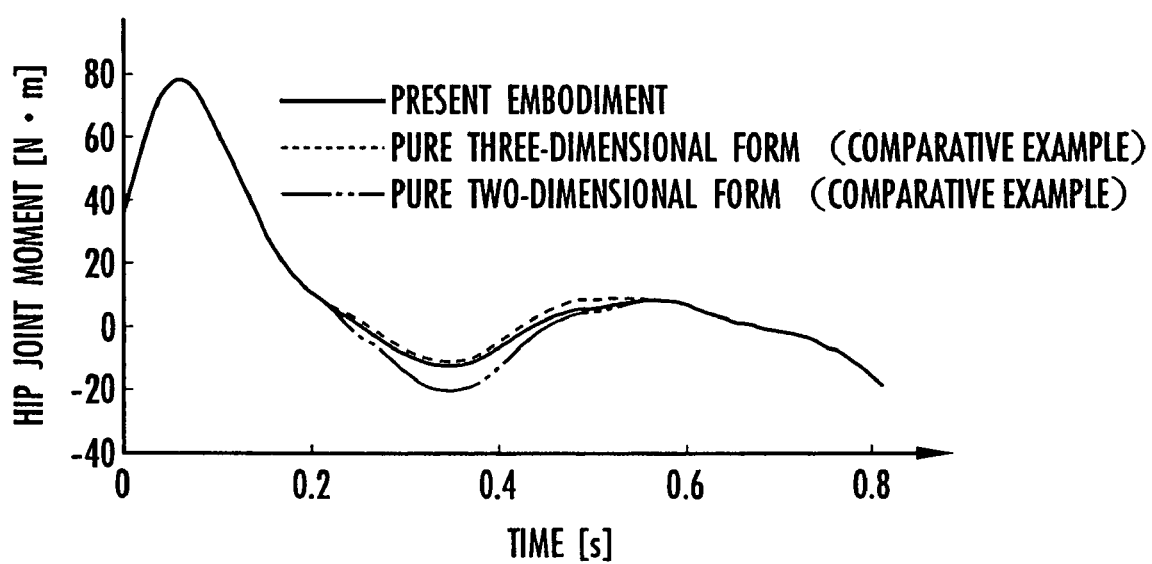

Referring now to FIG. 15 to FIG. 20, the results of verifying the advantages of the present embodiment will be explained. First, FIG. 15 and FIG. 16 are graphs respectively showing the time shifts of a hip joint moment and a knee joint moment when, for example, the human being 1 performs straight walking on a level ground at a moving speed of 4.5 km/h. The graphs indicated by the solid lines in these charts show the joint moments estimated in the present embodiment. The joint moments define their moments in the stretching direction of the legs 2 as positive. The graphs of two comparative examples for the comparison with the present embodiment are also shown by using the dashed lines and the chain double-dashed lines in FIG. 15 and FIG. 16. The graphs of the dashed lines illustrate a case where joint moments have been determined by constantly handling floor reaction force vectors, acceleration vectors, floor reaction force acting points, and the positions/postures of rigid elements as three-dimensional amounts (hereinafter referred to as the pure three-dimensional forms) without using the leg plane PL used in the aforesaid embodiment. The graphs of the chain double-dashed lines illustrate a case where joint moments have been determined by constantly handling floor reaction force vectors, acceleration vectors, floor reaction force acting points, and the positions/postures of rigid elements as two-dimensional amounts on a sagittal plane (a plane of a vertical posture observed sideways)(hereinafter referred to as the pure two-dimensional forms) as with an embodiment in Japanese Unexamined Patent Application Publication No. 2003-89083 previously proposed by the present applicant. The examples shown in FIG. 15 and FIG. 16 are both examples of a case where the human being 1 is walking straight primarily by bending/stretching motions of the legs 2 with little abduction, adduction or twist of the hip joint 9 of each leg 2. Thus, the rotational angles detected by the joint displacement sensor 11 of the hip joint 9 are mainly rotational angles about the axis substantially perpendicular to the leg plane PL of each leg 2 and the detection accuracy thereof is steadily relatively high.

As shown in these FIG. 15 and FIG. 16, the present embodiment and the pure three-dimensional form provide substantially the same joint moments. Therefore, it is understood that the present embodiment makes it possible to estimate joint moments with accuracy equivalent to the pure three-dimensional form, which is considered to allow joint moments that are highly accurate in principle to be obtained despite the arithmetic processing of the inverse dynamic model carried out two-dimensionally. Some joint moments obtained in the examples in the pure two-dimensional form exhibit relatively large differences from joint moments obtained in the pure three-dimensional form and the present embodiment. Hence, it is understood that the present embodiment makes it possible to estimate joint moments with higher accuracy than that in the conventional pure two-dimensional form.

Figure 17:
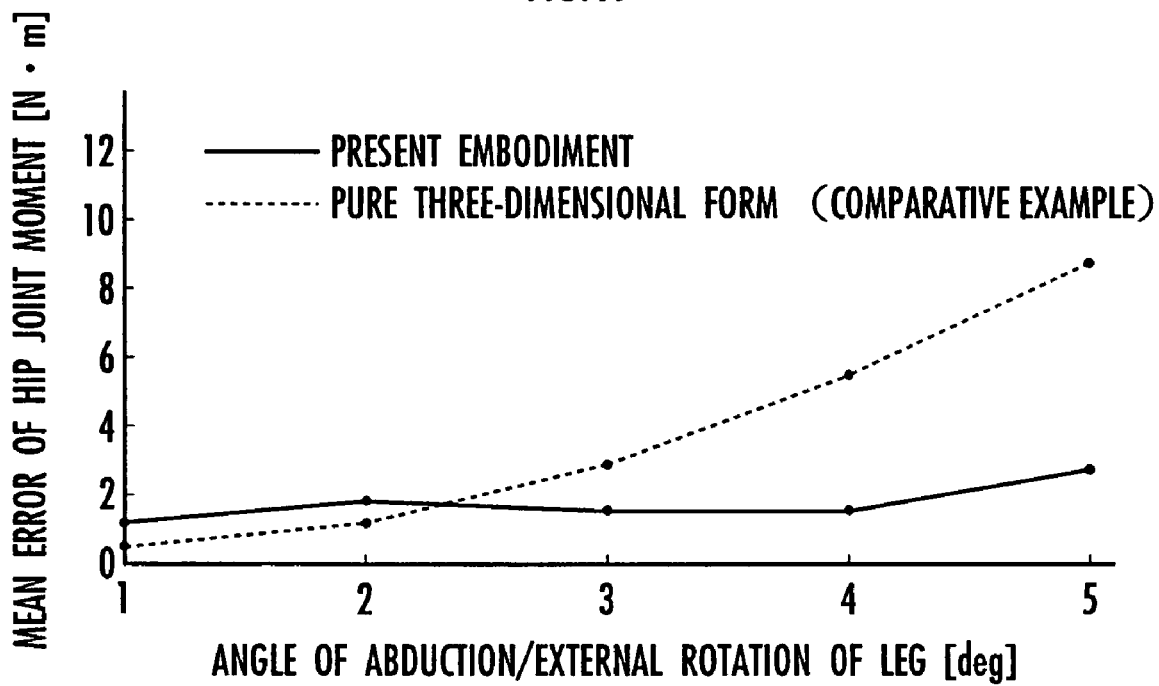
FIG. 17 is a graph showing a relationship between an abduction or external rotation angle of a leg and an error of an estimated value of a joint moment of a hip joint when the human being walks.
Figure 18:
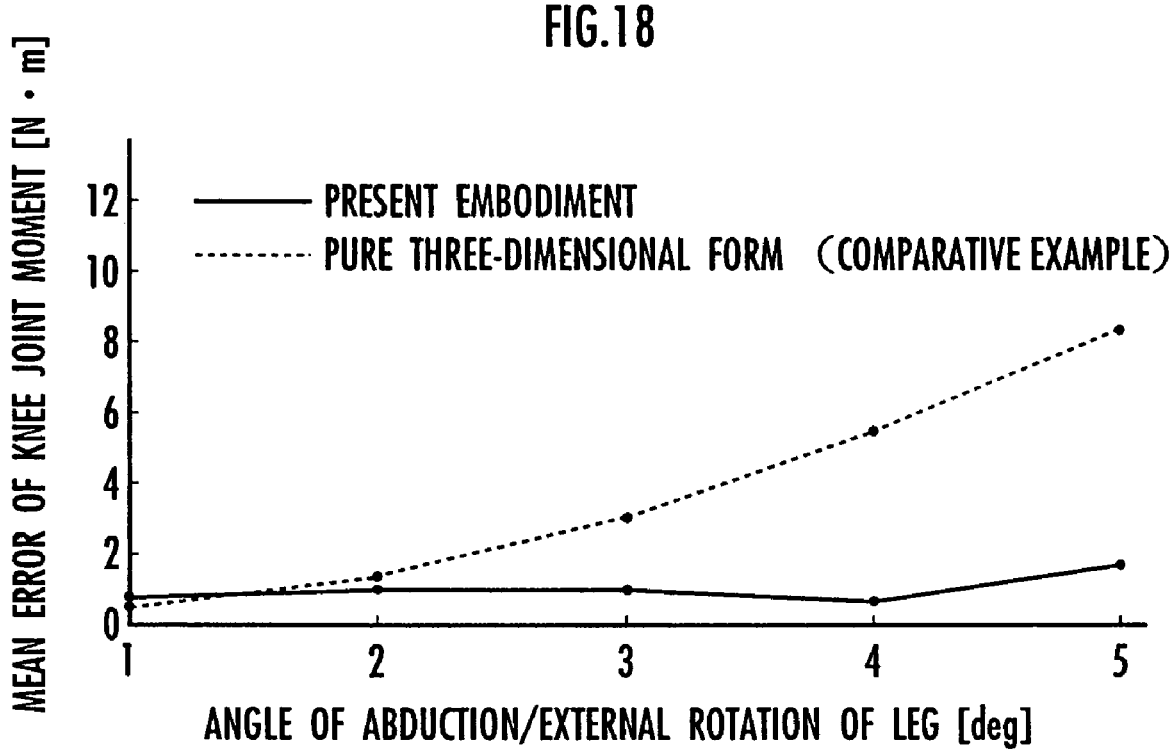
FIG. 18 is a graph showing a relationship between an abduction or external rotation angle of a leg and an error of an estimated value of a joint moment of a knee joint when the human being walks.

An explanation will now be given in conjunction with FIG. 17 to FIG. 20. FIG. 17 and FIG. 18 are graphs showing the average errors of the joint moments of the hip joint 9 and the knee joint 11 when the human being 1 walks straight (4.5 km/h) in a state wherein each leg 2 has been rotated from the aforesaid reference posture state by a plurality of different angles (1 deg, 2 deg, 3 deg, 4 deg and 5 deg in this example) in the direction of abduction (the direction in which the leg 2 is moved to a side of the human being 1) and in the direction of external rotation (the direction in which the leg 2 is moved about the axis of the thigh 12 such that the leading edge of the foot 14 of the leg 2 faces outward) at the hip joint 9 thereof, and further, in a state wherein the leg 2 has been rotated from the aforesaid reference posture state by a plurality of different angles (the same as the angles of the abduction and external rotation of the hip joint 9 in this example) in the direction of external rotation (the direction in which the leg 2 is moved about the axis of the crus 10 such that the leading edge of the foot 14 of the leg 2 faces outward) at the knee joint 11 thereof. Here, FIG. 17 is a graph related to the joint moments of the hip joint 9 and FIG. 18 is a graph related to the joint moments of the knee joint 11, and they show the average values of differences between the joint moments determined by the technique in accordance with the present embodiment and the values actually measured, using a torque meter or the like, by solid lines (average errors). In this case, in FIG. 17 and FIG. 18, each leg 2 is turned in both directions of abduction and external rotation at the hip joint 9 by each angle on the axis of abscissas, and the leg 2 is also turned in the direction of external rotation by the angle at the knee joint 11. When calculating the joint moments of the hip joint 9 and the knee joint 11, for the sake of convenience, the values of floor reaction forces determined in correspondence with FIG. 15 and FIG. 16 are used as substitutes. For comparison with the embodiment, the average errors of the joint moments determined by the technique of the aforesaid pure three-dimensional form are shown by dashed lines.

Figure 19:
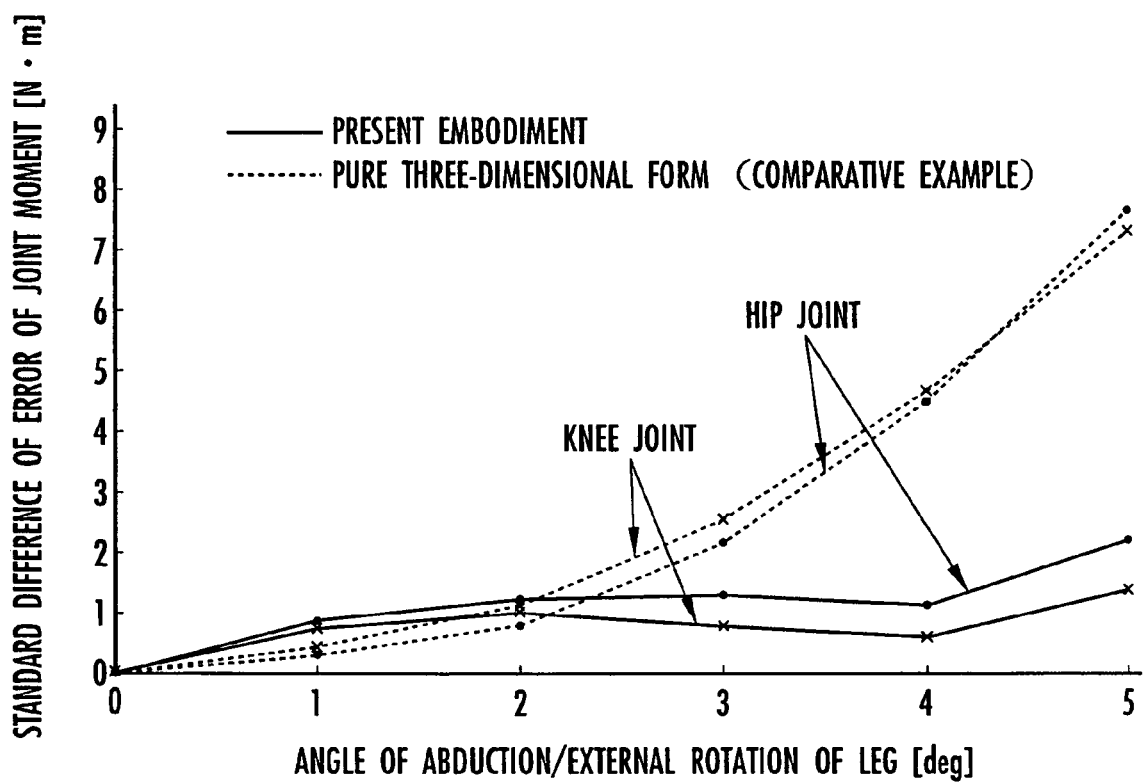
FIG. 19 is a graph showing a relationship between abduction or external rotation angles of a leg and standard differences of errors of estimated values of joint moments of a knee joint and a hip joint when the human being walks.
Figure 20:
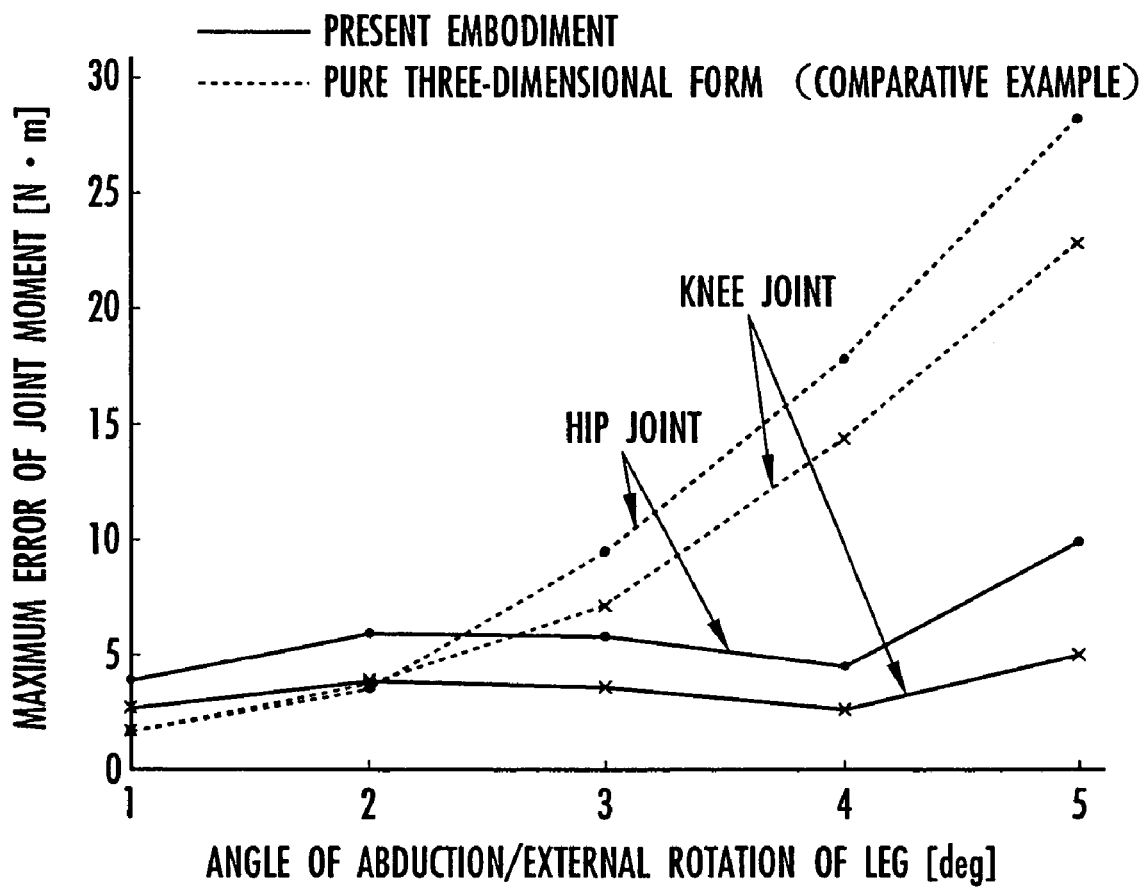
FIG. 20 is a graph showing a relationship between abduction or external rotation angles of a leg and maximum errors of estimated values of joint moments of a knee joint and a hip joint when the human being walks.

Further, FIG. 19 is a graph showing the standard differences of errors (the levels of variations centering around mean values) of the joint moments determined as described above in conjunction with FIG. 17 and FIG. 18. FIG. 20 is a graph showing the maximum values of errors of the joint moments determined as described above in conjunction with FIG. 17 and FIG. 18. In this case, these FIG. 19 and FIG. 20 show the ones by the technique of the present embodiment by the solid lines and the ones by the technique of the pure three-dimensional form by the dashed lines.

As shown in FIG. 17, FIG. 18 and FIG. 20, when the walking is performed in the state wherein the legs 2 have been subjected to abduction or external rotation, the technique of the present embodiment restrains the errors (average errors and maximum errors) of the joint moments of the knee joint 11 and the hip joint 9 to relatively small values regardless of the angles of abduction or the angles of external rotation of the legs 2. Moreover, as shown in FIG. 19, the technique of the present embodiment also restrains the standard differences of the errors, i.e., the levels of variations, of the joint moments of the knee joint 11 and the hip joint 9 to relatively small values regardless of the angles of abduction or the angles of external rotation of the legs 2. In other words, it is understood that joint moments can be estimated with stable accuracy. In comparison, according to the pure three-dimensional technique, if the angles of abduction or the angles of external rotation of the legs 2 are 2 deg or less, then the average errors and the maximum errors of the joint moments of the knee joint 11 and the hip joint 9 are smaller than or substantially equal to those in the present embodiment. However, if the angles of abduction or the angles of external rotation of the legs 2 are 3 deg or more, then the average errors and the maximum errors of the joint moments of the knee joint 11 and the hip joint 9 tend to be larger than those in the present embodiment, and the maximum errors of the joint moments of the hip joint 9, in particular, become considerably large. Further, according to the pure three-dimensional technique, if the angles of abduction or the angles of external rotation of the legs 2 are 3 deg or more, then the standard differences of the errors (the level of variations) of the joint moments of the knee joint 11 and the hip joint 9 also tend to be significantly large, as compared with the present embodiment. This is considered to be because, if the angles of abduction or the angles of external rotations of the legs 2 are relatively large, then the detection errors of the rotational angles of the hip joint 9 about an axis other than the axis in the direction perpendicular to the leg plane PL increase, and in the pure three-dimensional technique at this time, the detection errors exert significant influences in the final inverse dynamic arithmetic processing. The final inverse dynamic arithmetic processing (the processing of the joint moment estimating means 37) according to the present embodiment determines joint moments without using the rotational angles of the hip joint 9 about an axis other than the axis in the direction perpendicular to the leg plane PL, so that it is impervious to the influences of the detection errors of the angles of rotations of the hip joint 9 about an axis other than the axis in the direction perpendicular to the leg plane PL. As a result, it is considered that variations in the errors of the estimated values of joint moments hardly occur.

In addition, according to the aforesaid embodiment, to carry out the calculation processing of floor reaction force vectors and acceleration vectors as three-dimensional amounts, the arithmetic processing is implemented by using the body coordinate system BC as the basic coordinate system. Only the arithmetic processing of the floor reaction force acting point estimating means 35 is the arithmetic processing that considers the inclination angles relative to the vertical direction of the body coordinate system BC or the waist 6. This makes it possible to considerably reduce the arithmetic processing that uses the inclination angles of the waist 6 or the like with respect to the vertical direction, as compared with conventional techniques. As a result, even if it is difficult to grasp inclination angles with high accuracy, accumulation of errors can be minimized, leading to improved estimation accuracy of joint moments. Furthermore, using the floor reaction force acting point estimating means that does not use inclination angles obviates the need for providing a joint moment estimating system with a three-dimensional posture sensor or the like, allowing the system to be smaller and simplified.

INDUSTRIAL APPLICABILITY

As described above, the present invention makes it possible to estimate a joint moment about an axis perpendicular to a leg plane of a leg of a bipedal walking body with stability and high accuracy, so that the invention can be effectively utilized for an apparatus for assisting a human being with walking or for a similar application.

The invention claimed is:

1. A method of estimating a joint moment of a bipedal walking body, comprising:
   a first step for sequentially grasping the displacement amounts of a plurality of joints, including at least an ankle joint, a hip joint and a knee joint of each leg of a bipedal walking body;
   a second step for sequentially grasping the positions and/or postures of corresponding rigid bodies of the bipedal walking body that are associated with rigid elements of a rigid link model using at least the rigid link model, the rigid link model being established beforehand to express the bipedal walking body in the form of a link assembly composed of a plurality of the rigid elements and a plurality of joint elements and the grasped displacement amounts of the joints;
   a third step for grasping the acceleration of a preset reference point of the bipedal walking body by using at least an output of an acceleration sensor attached to a predetermined region of the bipedal walking body;
   a fourth step for sequentially grasping a floor reaction force acting on each leg and the position of an acting point of the floor reaction force, the grasped positions and/or the postures of the corresponding rigid bodies of the bipedal walking body, the floor reaction force and the position of the acting point of the floor reaction force being changeable every moment, the acceleration of the reference point, the floor reaction force, and the position of the acting point of the floor reaction force being used to estimate a joint moment acting on at least one joint of each leg,
   wherein at least the displacement amounts of the hip joint, the knee joint, and the ankle joint of each leg that are grasped in the first step include the amount of rotation about an axis substantially perpendicular to a leg plane as a plane passing through these three joints;
   fixedly setting a posture of a leg coordinate system to the leg plane;
   changing the posture of the leg coordinate system with respect to a body coordinate system that is fixedly set to the bipedal walking body; and
   measuring the hip joint displacement amount about three axes including an axis perpendicular to the leg plane, wherein the displacement amount of the hip joint is a three-dimensional amount, the positions and/or postures of the corresponding rigid bodies grasped in the second step include at least the positions and/or the postures of the corresponding rigid bodies of the leg on the leg plane,
   the acceleration of the reference point grasped in the third step and the floor reaction force and the position of the acting point of the floor reaction force grasped in the fourth step are three-dimensional amounts, and
   a component of a joint moment acting on at least one joint of the leg about the axis that is substantially perpendicular to the leg plane is estimated on the basis of an inverse dynamic model representing the relationship between the motions of the corresponding rigid bodies of the leg and the translational forces and the moments acting on the corresponding rigid bodies on the leg plane by using the two-dimensional amounts obtained by projecting at least the acceleration of the reference point, the floor reaction force, and the position of the acting point of the floor reaction force onto a leg plane related to the leg on the basis of a displacement amount of the hip joint of the leg, and the positions and/or the postures of the corresponding rigid bodies of the leg on the leg plane.

2. The method of estimating a joint moment of a bipedal walking body according to claim 1, wherein the acceleration of the reference point grasped in the third step, and the floor reaction force and the position of the acting point of the floor reaction force grasped in the fourth step are three-dimensional amounts expressed in terms of a body coordinate system set beforehand as a three-dimensional coordinate system fixed to one predetermined rigid element of the rigid link model.

3. The method of estimating a joint moment of a bipedal walking body according to claim 2, comprising:
   a fifth step for sequentially determining the position of the overall center-of-gravity of the bipedal walking body in the body coordinate system by using the displacement amounts of joints of the bipedal walking body grasped in the first step and by using the rigid link model,
   a sixth step for sequentially determining the acceleration of the overall center-of-gravity in the body coordinate system from the time series data of the position of the overall center-of-gravity and the acceleration of the origin of the body coordinate system grasped using at least an output of the acceleration sensor, and
   a seventh step for sequentially determining whether a motion state of the bipedal walking body is a one-leg supporting state in which only one of a pair of legs is in contact with the ground or a two-leg supporting state in which both legs are in contact with the ground,
   wherein, if the motion state of the bipedal walking body is the one-leg supporting state, then the fourth step estimates the value of a floor reaction force in the body coordinate system according to a dynamic equation of the overall center-of-gravity of the bipedal walking body expressed by the acceleration of the overall center-of-gravity determined in the sixth step, the total weight of the bipedal walking body, and the floor reaction force acting on the leg in contact with the ground; and if the motion state of the bipedal walking body is the two-leg supporting state, then the fourth step grasps the values of the floor reaction forces acting on the two legs, respectively, in the body coordinate system, on the basis of a dynamic equation of the overall center-of-gravity of the bipedal walking body expressed by the acceleration of the overall center-of-gravity determined in the sixth step, the total weight of the bipedal walking body, and the floor reaction force acting on the two legs, respectively, and an expression of the relationship between the relative position of a specific part of the leg with respect to the overall center-of-gravity of the bipedal walking body and a floor reaction force acting on the leg, which is established on the assumption that the floor reaction forces acting on the legs are the vectors acting toward the overall center-of-gravity of the bipedal walking body from the specific part specified beforehand in the vicinity of the bottom end of the leg.

4. The method of estimating a joint moment of a bipedal walking body according to claim 1, comprising:
an eighth step for sequentially grasping the inclination angle, relative to the vertical direction, of a corresponding rigid body of a bipedal walking body, which corresponds to one predetermined rigid element of the rigid link model,
a ninth step for determining whether each of the legs of the bipedal walking body is in contact with the ground, and
a tenth step for grasping the positional relationship among at least the overall center-of-gravity of the bipedal walking body, the ankle joint of each leg in contact with the ground, and the metatarsophalangeal joint of the foot portion of the leg, and the vertical position of the ankle joint by using the inclination angle grasped in the eighth step, a displacement amount of each joint of the bipedal walking body grasped in the first step, and the rigid link model,
wherein the fourth step estimates the position in a horizontal plane of the acting point of a floor reaction force acting on a leg on the basis of the positional relationship among the overall center-of-gravity, the ankle joint of each leg in contact with the ground and the metatarsophalangeal joint of the foot portion of the leg grasped in the tenth step, and also estimates the vertical position of the acting point of a floor reaction force acting on the leg on the basis of the vertical position of the ankle joint of the leg.

5. The method of estimating a joint moment of a bipedal walking body according to claim 4, wherein, if the overall center-of-gravity exists at the rear side of the bipedal walking body in the forward/backward direction with respect to the ankle joint of the leg in contact with the ground, then the fourth step estimates the position in the horizontal plane of the ankle joint of the leg as the position in the horizontal plane of the acting point of the floor reaction force acting on the leg, if the overall center-of-gravity exists at the front side of the bipedal walking body in the forward/backward direction with respect to the metatarsophalangeal joint of the foot portion of the leg in contact with the ground, then the fourth step estimates the position in the horizontal plane of the metatarsophalangeal joint of the foot portion of the leg as the position in the horizontal plane of the acting point of the floor reaction force acting on the leg, and if the overall center-of-gravity exists at the front side of the bipedal walking body in the longitudinal direction with respect to the ankle joint of the leg in contact with the ground and exists at the rear side with respect to the metatarsophalangeal joint of the foot portion of the leg, then the fourth step estimates the position of a point in the horizontal plane at which its longitudinal position agrees with the overall center-of-gravity position on a segment that connects the ankle joint and the metatarsophalangeal joint of the leg, as the position in the horizontal plane of the acting point of the floor reaction force acting on the leg.

6. The method of estimating a joint moment of a bipedal walking body according to claim 4, wherein the fourth step estimates the vertical position of the acting point of a floor reaction force acting on a leg in contact with the ground as the position away downward in the vertical direction by a predetermined value, which has been specified beforehand, from the vertical position of the ankle joint of the leg grasped in the tenth step.

7. The method of estimating a joint moment of a bipedal walking body according to claim 6, wherein whether each of a portion adjacent to a toe side and a portion adjacent to a heel side of a foot portion of a leg, which has been determined to be in contact with the ground, is in contact with the ground is determined in the ninth step, the vertical position of the ankle joint of the leg in contact with the ground and the vertical position of the metatarsophalangeal joint of the foot portion of the leg are grasped in the tenth step, and the fourth step estimates the vertical position of the acting point of the floor reaction force by using a vertical distance between the ankle joint and the metatarsophalangeal joint determined from the vertical position of the ankle joint and the vertical position of the metatarsophalangeal joint, which have been grasped in the tenth step, in place of the predetermined value if it is determined in the ninth step that only the portion adjacent to the toe side out of the portion adjacent to the toe side and the portion adjacent to the heel side of the foot portion is in contact with the ground.

* * * * *